US012661338B2

(12) United States Patent
Low et al.

(10) Patent No.: US 12,661,338 B2
(45) Date of Patent: Jun. 23, 2026

(54) HETEROCYCLIC COMPOUNDS AS MODULATORS OF BETA-CATENIN / TCF4 INTERACTION

(71) Applicant: AGENCY FOR SCIENCE, TECHNOLOGY AND RESEARCH, Singapore (SG)

(72) Inventors: Joo Leng Low, Singapore (SG); Weina Du, Singapore (SG); Ramanuj Dasgupta, Singapore (SG); Hao Fan, Singapore (SG); Tenzin Gocha, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 937 days.

(21) Appl. No.: 17/639,634

(22) PCT Filed: Sep. 3, 2020

(86) PCT No.: PCT/SG2020/050512
§ 371 (c)(1),
(2) Date: Mar. 2, 2022

(87) PCT Pub. No.: WO2021/045686
PCT Pub. Date: Mar. 11, 2021

(65) Prior Publication Data

US 2022/0288033 A1 Sep. 15, 2022

(30) Foreign Application Priority Data

Sep. 4, 2019 (SG) .......................... 10201908175Q

(51) Int. Cl.
*A61K 31/4196* (2006.01)
*A61K 31/454* (2006.01)
*A61P 35/00* (2006.01)

(52) U.S. Cl.
CPC ........ *A61K 31/4196* (2013.01); *A61K 31/454* (2013.01); *A61P 35/00* (2018.01)

(58) Field of Classification Search
CPC .... A61K 31/454; A61K 31/4196; A61P 35/00
See application file for complete search history.

(56) References Cited

U.S. PATENT DOCUMENTS

2009/0163545 A1* 6/2009 Goldfarb ................ A61K 31/13 514/688

FOREIGN PATENT DOCUMENTS

| | | | | |
|---|---|---|---|---|
| CN | 106619622 A | 5/2017 | | |
| JP | 2006522744 A | 10/2006 | | |
| JP | 2007530589 A | 11/2007 | | |
| WO | WO-2004089415 A2 * | 10/2004 | ............ | A61K 31/16 |
| WO | WO-2005/097758 A1 | 10/2005 | | |
| WO | WO-2010/003023 A2 | 1/2010 | | |
| WO | WO-2018/237084 A1 | 12/2018 | | |

OTHER PUBLICATIONS

Saidov et al., Visnik Farmatsii (2012), (4), 22-26 (Year: 2012).*

Lu (European Journal of Pharmacology, vol. 62, pp. 8-14, published 2009) (Year: 2009).*

Rostom (European Journal of Medicinal Chemistry vol. 139 pp. 263-279 published 2017) (Year: 2017).*

Saidov (Visnik Farmatsii vol. 4 pp. 22-26, published 2012) (Year: 2012).*

Wu et al., "Diverse Mechanisms of β-Catenin Deregulation in Ovarian Endometrioid Adenocarcinomas", Cancer Research, vol. 61, Nov. 15, 2001, pp. 8247-8255.

Hayes et al., "Genetic Changes of Wnt Pathway Genes are Common Events in Metaplastic Carcinomas of the Breast", Clin Cancer Res, vol. 14, No. 13, Jul. 1, 2008, pp. 4038-4044.

Gonsalves et al., "An RNAi-based Chemical Genetic Screen Identifies Three Small-molecule Inhibitors of the Wnt/wingless Signaling Pathway", PNAS, vol. 108, No. 15, Apr. 12, 2011, pp. 5954-5963.

Morin et al., "Activation of β-Catenin-Tcf Signaling in Colon Cancer by Mutations in β-Catenin or APC", Science, vol. 275, Mar. 21, 1997, pp. 1787-1790.

Rimm et al., "Frequent Nuclear/Cytoplasmic Localization of β-Catenin Without Exon 3 Mutations in Malignant Melanoma", American Journal of Pathology, vol. 154, No. 2, Feb. 1999, pp. 325-329.

Zurawel et al., "Sporadic Medulloblastomas Contain Oncogenic β-Catenin Mutations", Cancer Research, vol. 58, Mar. 1, 1998, pp. 896-899.

Voeller et al., "β-Catenin Mutations in Human Prostate Cancer", Cancer Research, vol. 58, Jun. 15, 1998, pp. 2520-2523.

(Continued)

*Primary Examiner* — George W Kosturko
(74) *Attorney, Agent, or Firm* — MARSHALL, GERSTEIN & BORUN LLP

(57) ABSTRACT

Provided herein are compounds that are useful for or methods of inhibiting β-catenin or disrupting the interaction between β-catenin and T-cell factor 4, which are useful in the treatment of diseases or health conditions, such as cancer, neurodegenerative, a metabolic disease, a cardiovascular disease, fibrosis, and a bone disease. In one aspect, the compounds have Formula 1 wherein $R^1$ is $—(CR^4_2)_mXR^5$; $R^2$ is alkyl, alkenyl, alkynyl, cycloalkyl, cycloalkenyl, heterocycloalkyl, heterocycloalkenyl, aryl, aralkyl, heteroaralkyl, or heteroaryl; and $R^3$ is $—(CR^6_2)_nR^7$.

(I)

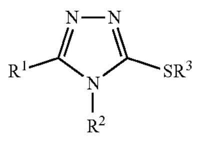

3 Claims, 21 Drawing Sheets

(56) References Cited

OTHER PUBLICATIONS

Schlosshauer et al., "Mutational Analysis of the CTNNB1 and APC Genes in Uterine Endometrioid Carcinoma", Modern Pathology, vol. 13, No. 10, May 19, 2000, pp. 1066-1071.
Mirabelli-Primdahl et al., "β-Catenin Mutations are Specific for Colorectal Carcinomas With Microsatellite Instability but Occur in Endometrial Carcinomas Irrespective of Mutator Pathway", Cancer Research, No. 59, Jul. 15, 1999, pp. 3346-3351.
Saegusa et al., "Frequent Nuclear β-Catenin Accumulation and Associated Mutations in Endometrioid-type Endometrial and Ovarian Carcinomas With Squamous Differentiation", Journal of Pathology, vol. 194, 2001, pp. 59-67.
Paul Polakis, "Wnt Signaling and Cancer", Genes & Development, vol. 14, 2000, pp. 1837-1851.
Koch et al., "Childhood Hepatoblastomas Frequently Carry a Mutated Degradation Targeting Box of the β-Catenin Gene", Cancer Res, vol. 59, No. 2, 1999, pp. 269-273.
Irwin et al., "Zinc: A Free Tool to Discover Chemistry for Biology", Journal of Chemical Information and Modeling, vol. 52, 2012, pp. 1757-1768.
Mysinger et al.", Directory of Useful Decoys, Enhanced (DUD-E): Better Ligands and Decoys for Better Benchmarking", Journal of Medicinal Chemistry, vol. 55, 2012, pp. 6582-6594.
Kuntz et al., "A Geometric Approach to Macromolecule-Ligand Interactions", J. Mol. Biol., vol. 161, 1982, pp. 269-288.
Mysinger et al., "Rapid Context-Dependent Ligand Desolvation in Molecular Docking", J. Chem. Inf. Model., vol. 50, 2010, pp. 1561-1573.
Fan et al., "Molecular Docking Screens Using Comparative Models of Proteins", J. Chem. Inf. Model, vol. 49, No. 11, Nov. 2009, pp. 2512-2527.
Graham et al., "The Crystal Structure of the β-Catenin/ICAT Complex Reveals the Inhibitory Mechanism of ICAT", Molecular Cell, vol. 10, Sep. 2002, pp. 563-571.
Poy et al., "Structure of a Human Tcf4-β-catenin Complex", Nature Structural Biology, vol. 8, No. 12, Dec. 2001, pp. 1053-1057.
Sampietro et al., "Crystal Structure of a β-Catenin/BCL9/Tcf4 Complex", Molecular Cell, vol. 24, Oct. 20, 2006, pp. 293-300.
Zhang et al., "Identification of Cavities on Protein Surface Using Multiple Computational Approaches for Drug Binding Site Prediction", Bioinformatics, vol. 27, No. 15, 2011, pp. 2083-2088.
Krivov et al., "Improved Prediction of Protein Side-chain Conformations With SCWRL4", Proteins, vol. 77, No. 4, Dec. 2009, pp. 778-795.
Sherman et al., "Novel Procedure for Modeling Ligand/Receptor Induced Fit Effects", J. Med. Chem., vol. 49, 2006, pp. 534-553.
Piccolo et al., The Biology of YAP/TAZ: Hippo Signaling and Beyond, Physiol Rev, vol. 94, 2014, pp. 1287-1312.
Fasolini et al., "Hot spots in Tcf4 for the Interaction With B-Catenin", The Journal of Biological Chemistry, vol. 278, No. 23, Jun. 6, 2003, pp. 21092-21098.
Liu et al., "Functional Interaction Between Peroxisome Proliferator-Activated Receptor γ and β-Catenin", Molecular and Cellular Biology, vol. 26, No. 15, Aug. 2006, pp. 5827-5837.
Michael Kahn, "Can We Safely Target the WNT Pathway?", Nat Rev Drug Discov., vol. 13, No. 7, Jul. 2014, pp. 513-532.
Written Opinion in SG Application No. 11202201332V dated Jul. 24, 2022, 9 pages.
First Office Action in JP Application No. 2022-513284, dated Sep. 10, 2024, 8 pages.
Peterson et al., "Discovery of Geranylgeranyltransferase-I Inhibitors With Novel Scaffolds by the Means of Quantitative Structure-Activity Relationship Modeling, Vitrual Screening, and Experimental Validation", Journal of Medicinal Chemistry, vol. 52, No. 14, Jul. 23, 2009, pp. 4210-4220.
Low et al., "Molecular Docking-aided Identification of Small Molecule Inhibitors Targeting β-catenin-TCF4 Interaction", iScience, vol. 24, No. 6, Jun. 25, 2021, 27 pages.
Extended European Search Report in EP Application No. 20859897.9 dated Jul. 14, 2023, 8 pages.
First Office Action in CN Application No. 202080060512.0 dated Feb. 29, 2024, 38 pages.
Pu et al., "Discovery of New Dual Binding TNKS Inhibitors of Wnt Signaling Inhibition by Pharmacophore Modeling, Molecular Docketing and Bioassay", Mol. BioSyst., vol. 13, Dec. 31, 2017, pp. 363-370.
STN Search Report, ACS, STN Registry Database, Apr. 1, 2018, 7 pages.
Second Office Action in CN Application No. 202080060512.0 dated Jul. 4, 2024, 48 pages.
Second Written Opinion in SG Application No. 11202201332V dated Dec. 5, 2023, 9 pages.
Dodge et al., "Diverse Chemical Scaffolds Support Direct Inhibition of the Membrane-bound O-Acyltransferase Porcupine", J. Biol. Chem., vol. 287, No. 27, Jun. 29, 2012, pp. 23246-23254.
Search Report and Written Opinion in International Application No. PCT/SG2020/050512 dated Dec. 28, 2020, 16 pages.
Second Office Action in EP Application No. 20859897.9 dated Jul. 18, 2025, 6 pages.
Office Action in JP Application No. 2022-513284 dated Feb. 18, 2025, 4 pages.

* cited by examiner iCRT3

GB8679

GB6853

GB1874

| Compound ID | Name | DOCK 1 | RANK 2 | HUMAN 3 | Final Score[4] | STF $IC_{50}$ (μM)[5] |
|---|---|---|---|---|---|---|
| C00010001 | iCRT 3 | 23 | 4 | 1 | * | 27 |
| B00011001 | A01 | 19 | 31 | -1 | * | > 100 |
| *B00010002* | *A02* | *51* | *24* | *1* | * | *nd* |
| *B00010003* | *A03* | *17* | *3* | *1* | *** | *62.29* |
| *B00012004* | *A04* | *29* | *25* | *1* | * | *> 100* |
| *B00010005* | *A05* | *39* | *5* | *1* | * | *nd* |
| *B00010006* | *A06* | *22* | *9* | *1* | ** | *37.28* |
| *B00011007* | *A07* | *12* | *49* | *-1* | * | *> 100* |
| *B00010008* | *A08* | *28* | *53* | *-1* | | *nd* |
| *B00010009* | *A09* | *35* | *2* | *1* | ** | *nd* |
| *B00011010* | *A10* | *11* | *22* | *-1* | * | *nd* |
| *B00010011* | *A11* | *41* | *48* | *-1* | | *v* |
| *B00010012* | *A12* | *34* | *10* | *1* | * | *9.62* |
| *B00012013* | *A13* | *21* | *14* | *1* | ** | *nd* |
| *B00010014* | *A14* | *42* | *38* | *0* | | *> 100* |
| *B00010015* | *A15* | *37* | *6* | *1* | * | *nd* |
| *B00011016* | *A16* | *26* | *37* | *1* | * | *nd* |
| *B00010017* | *A17* | *40* | *63* | *-1* | | *nd* |
| *B00010018* | *A18* | *57* | *11* | *1* | * | *nd* |
| *B00012019* | *A19* | *7* | *21* | *-1* | * | *nd* |

Fig. 5

| Compound ID | Name | DOCK 1 | RANK 2 | HUMAN 3 | Final Score4 | STF IC50 (µM)5 |
|---|---|---|---|---|---|---|
| B00010020 | A20 | 52 | 27 | -1 | | nd |
| B00010021 | A21 | 55 | 16 | 0 | | nd |
| B00012022 | A22 | 13 | 57 | 0 | * | nd |
| B00010023 | A23 | 50 | 52 | 0 | | nd |
| B00010024 | A24 | 48 | 30 | -1 | | nd |
| B00012025 | A25 | 4 | 43 | -1 | * | nd |
| B00010026 | A26 | 59 | 39 | -1 | | nd |
| B00010027 | A27 | 47 | 35 | -1 | | nd |
| B00012028 | A28 | 8 | 40 | -1 | * | nd |
| B00010029 | A29 | 60 | 15 | -1 | | nd |
| B00010030 | A30 | 56 | 61 | -1 | | nd |
| B00012031 | A31 | 16 | 7 | -1 | * | nd |
| B00010032 | A32 | 53 | 60 | -1 | | nd |
| B00010033 | A33 | 54 | 46 | -1 | | nd |
| B00012034 | A34 | 36 | 29 | -1 | | nd |
| B00010035 | A35 | 63 | 36 | -1 | | nd |
| B00010036 | A36 | 14 | 18 | -1 | * | nd |
| B00012037 | A37 | 1 | 17 | -1 | * | nd |
| B00010038 | A38 | 46 | 8 | -1 | | nd |
| B00010039 | A39 | 25 | 55 | -1 | | nd |
| B00012040 | A40 | 2 | 54 | -1 | * | nd |

Fig. 5 (Continued)

| Compound ID | Name | DOCK 1 | RANK 2 | HUMAN 3 | Final Score4 | STF IC50 (μM)5 |
|---|---|---|---|---|---|---|
| B00010041 | A41 | 45 | 45 | -1 | | nd |
| B00010042 | A42 | 62 | 51 | 0 | | nd |
| B00012043 | A43 | 31 | 50 | -1 | | nd |
| B00010044 | A44 | 61 | 47 | 0 | | nd |
| B00010045 | A45 | 3 | 23 | 1 | ** | 0.23 |
| B00011046 | A46 | 18 | 13 | 1 | ** | nd |
| B00010047 | A47 | 33 | 64 | -1 | | nd |
| B00010048 | A48 | 9 | 32 | 1 | ** | 2.84 |
| B00011049 | A49 | 43 | 58 | 1 | * | nd |
| B00010050 | A50 | 44 | 19 | 1 | * | nd |
| B00010051 | A51 | 32 | 20 | 1 | * | > 100 |
| B00010052 | A52 | 20 | 44 | 1 | ** | > 100 |
| B00010053 | A53 | 27 | 33 | -1 | | > 100 |
| B00010054 | A54 | 58 | 34 | -1 | | nd |
| B00010055 | A55 | 15 | 12 | -1 | * | nd |
| B00010056 | A56 | 38 | 41 | -1 | | nd |
| B00010057 | A57 | 10 | 28 | 1 | ** | nd |
| B00010058 | A58 | 24 | 42 | -1 | | nd |
| B00010059 | A59 | 64 | 56 | 0 | | nd |
| B00010060 | A60 | 49 | 1 | -1 | * | nd |
| B00010061 | A61 | 6 | 26 | 0 | * | nd |
| B00010062 | A62 | 5 | 59 | -1 | * | nd |
| B00010063 | A63 | 30 | 62 | -1 | | nd |

Fig. 5 (Continued)

| Compound Index | DOCK energy score |
|---|---|
| GB2880 | -59.37 |
| GB8752 | -54.84 |
| GB9694 | -54.56 |
| GB1068 | -53.79 |
| GB5078 | -53.39 |
| GB1874 | -52.93 |
| GB8845 | -51.02 |
| GB2955 | -50.47 |
| GB1856 | -50.45 |
| GB2082 | -50.11 |
| GB0985 | -49.85 |
| GB1317 | -49.72 |
| GB8679 | -48.84 |
| GB1281 | -48.78 |
| GB2331 | -48.69 |
| GB5400 | -48.63 |
| GB0993 | -48.54 |
| GB7770 | -48.18 |
| GB5462 | -47.89 |
| GB1723 | -47.83 |
| GB0685 | -47.35 |
| GB0768 | -47.35 |
| GB7455 | -47.21 |
| GB5898 | -47.06 |
| GB5855 | -47.04 |
| GB6853 | -46.56 |
| GB4096 | -46.54 |

Fig. 6A

| | |
|---|---|
|  iCRT3 |  GB2880 |
|  GB5078 |  GB7455 |
|  GB2331 |  GB5400 |
|  GB8679 |  GB8752 |
|  GB2082 |  GB5855 |
|  GB6853 |  GB2955 |
|  GB8845 |  GB0685 |

| | |
|---|---|
|  GB0985 |  GB5462 |
|  GB9694 |  GB1317 |
|  GB0768 |  GB1723 |
|  GB4096 |  GB1856 |
|  GB1068 |  GB1874 |
|  GB0993 |  GB7770 |
|  GB1281 |  GB5898 |

HETEROCYCLIC COMPOUNDS AS MODULATORS OF BETA-CATENIN / TCF4 INTERACTION

CROSS REFERENCE TO RELATED APPLICATIONS

This application claims the benefit of priority of Singapore Patent Application Number 10201908175Q, filed on 4 Sep. 2019, which is hereby incorporated by reference in its entirety.

TECHNICAL FIELD

The present disclosure generally relates to methods of inhibiting the Wnt/β-catenin (β-cat) signalling pathways. More particularly the present disclosure provides small molecule inhibitors of the β-cat/T-cell factor 4 (TCF4), interaction resulting in attenuation of downstream Wnt expression. The compounds and methods provided herein are useful in the treatment, management, or prevention of diseases ameliorated by inhibiting the interaction of β-cat and TCF4, such as cancer, neurodegenerative, metabolic diseases, a cardiovascular disease, fibrosis, and bone diseases.

BACKGROUND

The canonical Wnt/β-cat signalling pathway is an important signal transduction pathway required for proper embryonic development and adult tissue self-renewal. Activation of the pathway occurs through the binding of Wnt ligand proteins to Frizzled and low-density lipoprotein receptor-related protein 6 (LRP6). In the absence of Wnt activation, the destruction complex comprising of Axin, casein kinase 1α (CK1α), glycogen synthase kinase 3β (GSK3β), and adenomatous polyposis coli (APC) phosphorylates β-cat, the key nuclear effector of Wnt signalling, and targets it for ubiquitination and proteasomal degradation. Upon activation of the pathway by the Wnt ligand results in the recruitment of the destruction complex, to the membrane, resulting in its inactivation. Inhibition of the destruction complex leads to the cytoplasmic accumulation of non-phosphorylated β-cat and its subsequent translocation to the nucleus where it binds to the lymphoid enhancer factor/T-cell factor (LEF/TCF) family transcription factors, along with a host of other co-factors including Bcl-9 and Pygopus, to activate downstream target gene expression.

Due to its importance in maintaining tissue homeostasis, aberrant activation of the Wnt pathway, especially in stem cells often serves as a driver of disease, such as cancer. In particular it has been well established that in the majority of colorectal cancers (CRC), loss of function of the APC tumour suppressor gene is an early driver of tumorigenesis, resulting in the formation of adenomas. Additionally loss of function mutations in Axin2 and activating mutations in β-cat are prevalent in hepatocellular carcinomas (HCC), although they can also be found in CRCs at lower frequencies. Apart from cancer, misregulation of the Wnt pathway is also implicated in the development of diseases such as neurodegenerative, metabolic, and bone disease. Consequently numerous Wnt pathway targeting agents including small molecule inhibitors, and the antibody-based therapeutics have been reported over the years. Despite the large number of promising discoveries for Wnt-targeting drug entities, most have failed to proceed to human clinical trials. There have been isolated examples of small molecule inhibitors that have made it to Phase I trials; however none have been approved so far for clinical use. One challenge faced by these agents in their development as therapeutics is that there is significant crosstalk between the Wnt signalling pathway and other pathways such as Notch and Hedgehog. Crosstalk between the pathways could limit the specificity of these agents or could affect their efficacy in treatment response through compensatory activation. In addition, driver mutations in various components within the linear cascade of the Wnt pathway could also limit the pathway inhibitory efficacy of these agents.

Consequently, it is predicted that effective and specific downregulation of the Wnt pathway can be achieved by inhibiting the β-cat-TCF4 interaction, which is required for downstream Wnt target gene expression. The advantage of this strategy is two-fold. First, targeting the β-cat-TCF4 interaction would be more efficacious in diseases where mutations are present in the downstream components of the Wnt pathway thereby rendering upstream inhibitors less effective. Second, this strategy would specifically target the transcriptional function of β-cat without affecting its interaction with E cadherin (ECAD) at the cell-cell adherens junctions (AJs). It is proposed that specificity could be achieved by selectively targeting the β-cat-TCF4 binding pocket that is distinct from the β-cat-ECAD binding pocket.

A cell-based RNA interference (RNAi)-based chemical genetic screen was previously reported that identified compounds that inhibit β-cat-TCF4 interaction. From the screen, 3 compounds; iCRT3, iCRT5, and iCRT14, were found that can disrupt the β-cat-TCF4 interaction without affecting β-cat's interaction with ECAD. In silico docking of iCRT3 onto β-cat predicted that iCRT3 binds to the site on β-cat that binds to the extended region of TCF4 (residues 13-25). This predicted iCRT3 binding site on β-cat is lined by Arg469 and Lys435 that forms a salt bridge with Asp16 of TCF4 and is critical for the high affinity of TCF4 to β-cat. Due to the importance of this binding pocket with respect to the β-cat-TCF4 interaction, over the years it has served as an attractive target site for in silico docking studies to identify inhibitors of β-cat-TCF4 interaction.

There thus exists a need for improved methods for inhibiting the β-cat-TCF4 interaction and attendant attenuation of downstream Wnt signalling that address or overcome at least some of the aforementioned challenges.

There also exists the need for therapeutic agents that are able to treat a disease or health condition that is ameliorated by inhibiting β-cat or disrupting the interaction between β-cat and TCF4.

SUMMARY

Using existing protein x-ray crystal structures and biological activities of known β-cat-TCF4 interaction inhibitors, here a computational model is described that better predicts potential small molecule inhibitors of this protein-protein interaction surface. To demonstrate the predictability of the computational model system, in silico screening of a library of small molecules was carried out and identified 27 compounds as potential binders to β-cat. Experimental validation of the hit compounds identified 3 potent inhibitors of Wnt reporter activity of which compound GB1874 was found to elicit robust Wnt tumor inhibitory phenotypes both in vitro and in vivo phenotypic assays. Based on these results and further in silico and biological screening, a family of compounds that strongly inhibit Wnt reporter activity were identified.

In one aspect, provided herein is use of a compound in the manufacture of a medicament for the treatment of a disease or health condition that is ameliorated by inhibiting β-catenin (β-cat) or disrupting the interaction between β-cat and T-cell factor 4 (TCF4), wherein the compound has Formula 1:

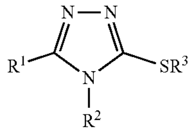

1 or a pharmaceutically acceptable salt thereof, wherein $R^1$ is —$(CR^4_2)_m XR^5$;

$R^2$ is alkyl, alkenyl, alkynyl, cycloalkyl, cycloalkenyl, heterocycloalkyl, heterocycloalkenyl, aryl, aralkyl, heteroaralkyl, or heteroaryl;

$R^3$ is —$(CR^6_2)_n R^7$;

$R^4$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl; or two instances of $R^4$ taken together with the carbon or carbons to which they are attached form a 3-7 membered cycloalkyl;

$R^5$ is hydrogen, cycloalkyl, cycloalkenyl, heterocycloalkyl, heterocycloalkenyl, aryl, or heteroaryl;

$R^6$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl; or two instances of $R^6$ taken together with the carbon or carbons to which they are attached form a 3-7 membered cycloalkyl;

$R^7$ is —(C═O)$R^8$, —(C═O)O$R^8$, or —(C═O)N$(R^8)_2$; or $R^7$ is a moiety having Formula 2:

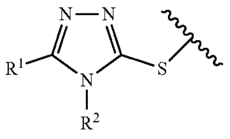

2

$R^8$ for each occurrence is independently selected from the group consisting of alkyl, alkenyl, alkynyl, cycloalkyl, cycloalkenyl, heterocycloalkyl, heterocycloalkenyl, aryl, heteroaryl, aralkyl, and heteroaralkyl; or two $R^8$ taken together with the nitrogen to which they are attached form a 3-7 membered heterocycloalkyl; or $R^6$ and $R^8$ taken together with the atoms to which they are attached form a 4-7 membered optionally substituted cycloalkyl or a 4-7 membered optionally substituted heterocycloalkyl;

m is a whole number selected from 0-4;

n is a whole number selected from 0-4; and

X is —O—, —S—, or is absent.

In another aspect, provided herein is a method of inhibiting β-cat or disrupting the interaction between β-cat and TCF4, the method comprising: contacting β-cat with a compound of Formula 1:

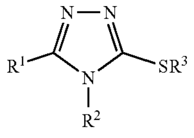

1 or a pharmaceutically acceptable salt thereof, wherein $R^1$ is —$(CR^4_2)_m XR^5$;

$R^2$ is alkyl, alkenyl, alkynyl, cycloalkyl, cycloalkenyl, heterocycloalkyl, heterocycloalkenyl, aryl, aralkyl, heteroaralkyl, or heteroaryl;

$R^3$ is —$(CR^6_2)_n R^7$;

$R^4$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl; or two instances of $R^4$ taken together with the carbon or carbons to which they are attached form a 3-7 membered cycloalkyl;

$R^5$ is hydrogen, cycloalkyl, cycloalkenyl, heterocycloalkyl, heterocycloalkenyl, aryl, or heteroaryl;

$R^6$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl; or two instances of $R^6$ taken together with the carbon or carbons to which they are attached form a 3-7 membered cycloalkyl;

$R^7$ is —(C═O)$R^8$, —(C═O)O$R^8$, or —(C═O)N$(R^8)_2$; or $R^7$ is a moiety having Formula 2:

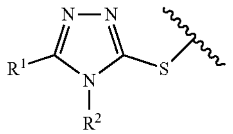

2

$R^8$ for each occurrence is independently selected from the group consisting of alkyl, alkenyl, alkynyl, cycloalkyl, cycloalkenyl, heterocycloalkyl, heterocycloalkenyl, aryl, heteroaryl, aralkyl, and heteroaralkyl; or two $R^8$ taken together with the nitrogen to which they are attached form a 3-7 membered heterocycloalkyl; or $R^6$ and $R^8$ taken together with the atoms to which they are attached form a 4-7 membered optionally substituted cycloalkyl or a 4-7 membered optionally substituted heterocycloalkyl;

m is a whole number selected from 0-4;

n is a whole number selected from 0-4; and

X is —O—, —S—, or is absent.

In another aspect, provided herein is a method of treating a disease or health condition that is ameliorated by inhibiting β-cat or disrupting the interaction between β-cat and TCF4 in a subject in need thereof, the method comprising administering a therapeutically effective amount of a compound of Formula 1:

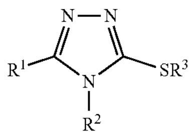

1 or a pharmaceutically acceptable salt thereof, wherein $R^1$ is —$(CR^4_2)_mXR^5$;

$R^2$ is alkyl, alkenyl, alkynyl, cycloalkyl, cycloalkenyl, heterocycloalkyl, heterocycloalkenyl, aryl, aralkyl, heteroaralkyl, or heteroaryl;

$R^3$ is —$(CR^6_2)_nR^7$;

$R^4$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl; or two instances of $R^4$ taken together with the carbon or carbons to which they are attached form a 3-7 membered cycloalkyl;

$R^5$ is hydrogen, cycloalkyl, cycloalkenyl, heterocycloalkyl, heterocycloalkenyl, aryl, or heteroaryl;

$R^6$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl; or two instances of $R^6$ taken together with the carbon or carbons to which they are attached form a 3-7 membered cycloalkyl;

$R^7$ is —(C═O)$R^8$, —(C═O)O$R^8$, or —(C═O)N$(R^8)_2$; or $R^7$ is a moiety having Formula 2:

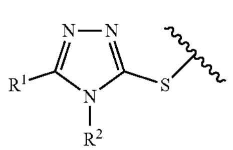

2

$R^8$ for each occurrence is independently selected from the group consisting of alkyl, alkenyl, alkynyl, cycloalkyl, cycloalkenyl, heterocycloalkyl, heterocycloalkenyl, aryl, heteroaryl, aralkyl, and heteroaralkyl; or two $R^8$ taken together with the nitrogen to which they are attached form a 3-7 membered heterocycloalkyl; or $R^6$ and $R^8$ taken together with the atoms to which they are attached form a 4-7 membered optionally substituted cycloalkyl or a 4-7 membered optionally substituted heterocycloalkyl;

m is a whole number selected from 0-4;

n is a whole number selected from 0-4; and

X is —O—, —S—, or is absent.

In another aspect, provided herein is a compound for use in treating a disease or health condition that is ameliorated by inhibiting β-cat or disrupting the interaction between β-cat and TCF4, wherein the compound has Formula 1:

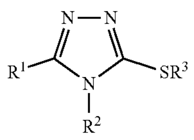

1 or a pharmaceutically acceptable salt thereof, wherein $R^1$ is —$(CR^4_2)_mXR^5$;

$R^2$ is alkyl, alkenyl, alkynyl, cycloalkyl, cycloalkenyl, heterocycloalkyl, heterocycloalkenyl, aryl, aralkyl, heteroaralkyl, or heteroaryl;

$R^3$ is $(CR^6_2)_nR^7$;

$R^4$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl; or two instances of $R^4$ taken together with the carbon or carbons to which they are attached form a 3-7 membered cycloalkyl;

$R^5$ is hydrogen, cycloalkyl, cycloalkenyl, heterocycloalkyl, heterocycloalkenyl, aryl, or heteroaryl;

$R^6$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl; or two instances of $R^6$ taken together with the carbon or carbons to which they are attached form a 3-7 membered cycloalkyl;

$R^7$ is —(C═O)$R^8$, —(C═O)O$R^8$, or —(C═O)N$(R^8)_2$; or $R^7$ is a moiety having Formula 2:

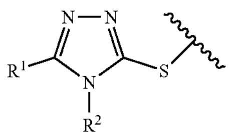

2

$R^8$ for each occurrence is independently selected from the group consisting of alkyl, alkenyl, alkynyl, cycloalkyl, cycloalkenyl, heterocycloalkyl, heterocycloalkenyl, aryl, heteroaryl, aralkyl, and heteroaralkyl; or two $R^8$ taken together with the nitrogen to which they are attached form a 3-7 membered heterocycloalkyl; or $R^6$ and $R^8$ taken together with the atoms to which they are attached form a 4-7 membered cycloalkyl or 4-7 heterocycloalkyl;

m is a whole number selected from 0-4;

n is a whole number selected from 0-4; and

X is —O—, —S—, or is absent.

In another aspect, provided herein is a compound for use in therapy, wherein the compound has Formula 1:

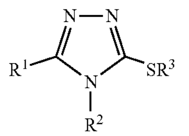

1 or a pharmaceutically acceptable salt thereof, wherein $R^1$ is —$(CR^4_2)_mXR^5$;

$R^2$ is alkyl, alkenyl, alkynyl, cycloalkyl, cycloalkenyl, heterocycloalkyl, heterocycloalkenyl, aryl, aralkyl, heteroaralkyl, or heteroaryl;

$R^3$ is —$(CR^6_2)_nR^7$;

$R^4$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl;

or two instances of $R^4$ taken together with the carbon or carbons to which they are attached form a 3-7 membered cycloalkyl;

$R^5$ is hydrogen, cycloalkyl, cycloalkenyl, heterocycloalkyl, heterocycloalkenyl, aryl, or heteroaryl;

$R^6$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl; or two instances of $R^6$ taken together with the carbon or carbons to which they are attached form a 3-7 membered cycloalkyl;

$R^7$ is —(C=O)$R^8$, —(C=O)O$R^8$, or —(C=O)N($R^8$)$_2$; or $R^7$ is a moiety having Formula 2:

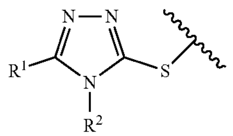

2

$R^8$ for each occurrence is independently selected from the group consisting of alkyl, alkenyl, alkynyl, cycloalkyl, cycloalkenyl, heterocycloalkyl, heterocycloalkenyl, aryl, heteroaryl, aralkyl, and heteroaralkyl; or two $R^8$ taken together with the nitrogen to which they are attached form a 3-7 membered heterocycloalkyl; or $R^6$ and $R^8$ taken together with the atoms to which they are attached form a 4-7 membered optionally substituted cycloalkyl or a 4-7 membered optionally substituted heterocycloalkyl;

m is a whole number selected from 0-4;

n is a whole number selected from 0-4; and

X is —O—, —S—, or is absent.

BRIEF DESCRIPTION OF DRAWINGS

The above and other objects and features of the present disclosure will become apparent from the following description of the disclosure, when taken in conjunction with the accompanying drawings.

FIG. 2 depicts an in silico investigation of predicted compounds for Wnt signaling inhibition.

FIG. 3 depicts the effect of hit compounds on HCT116 cells via the Wnt signaling pathway.

FIG. 4 depicts the inhibit growth by hit compounds and their effects on stemness of Wnt driven cells.

FIG. 5 depicts in silico predicted docking scores and in vitro cell based $IC_{50}$ values for analogues of iCRT. Lower DOCK score, better predicted binding. Lower RANK score, better predicted binding. Favorable (1), neutral (0), unfavorable (−1). More (*) higher ranking. nd=Not determined.

FIG. 6A depicts DOCK scores of top 27 compounds identified from the Enamine pharmacological diversity compound library.

Figure 6B:
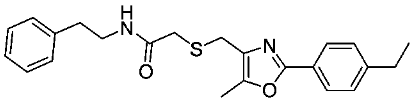
Figure 6B:
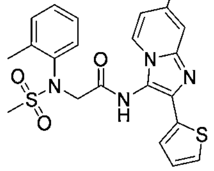
Figure 6B:
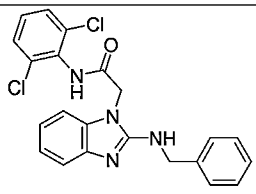
Figure 6B:
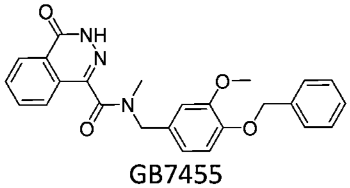
Figure 6B:
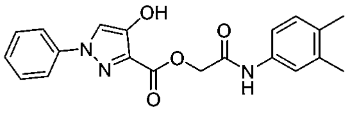
Figure 6B:
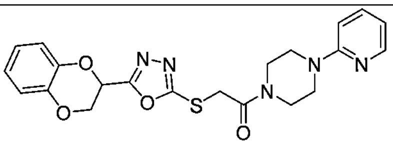
Figure 6B:
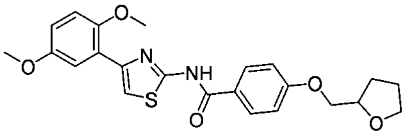
Figure 6B:
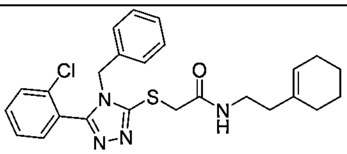
Figure 6B:
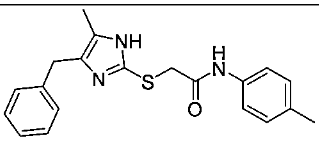
Figure 6B:
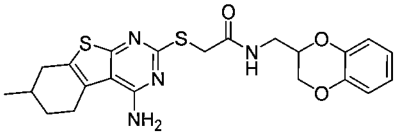
Figure 6B:
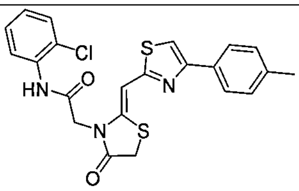
Figure 6B:
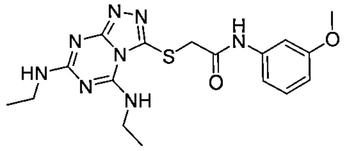
Figure 6B:
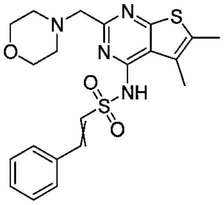
Figure 6B:
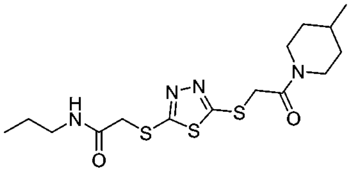
Figure 6B:
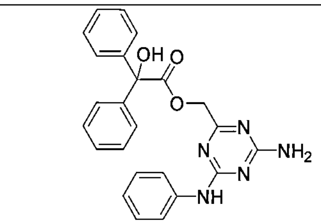
Figure 6B:
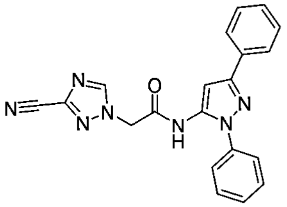
Figure 6B:
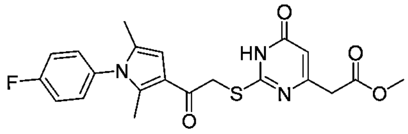
Figure 6B:
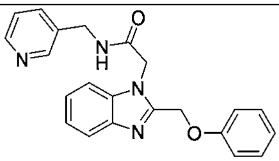
Figure 6B:
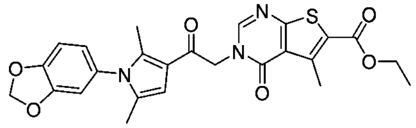
Figure 6B:
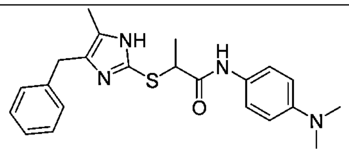
Figure 6B:
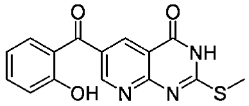
Figure 6B:
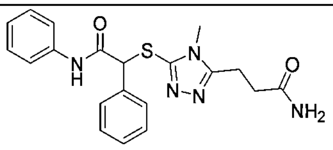
Figure 6B:
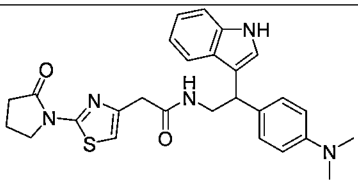
Figure 6B:
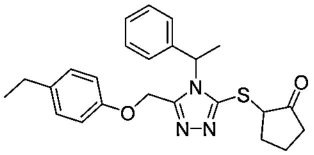
Figure 6B:
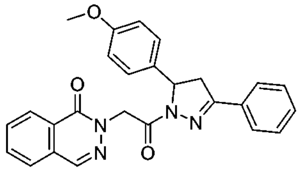
Figure 6B:
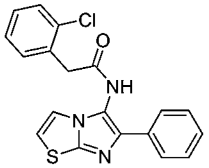
Figure 6B:
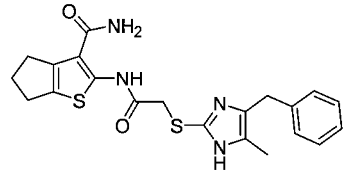
Figure 6B:
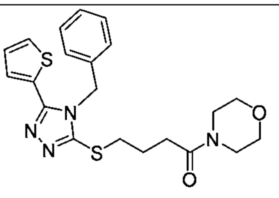

FIG. 6B depicts the structures of the top 27 compounds identified from the Enamine pharmacological diversity compound library.

Figure 7A:
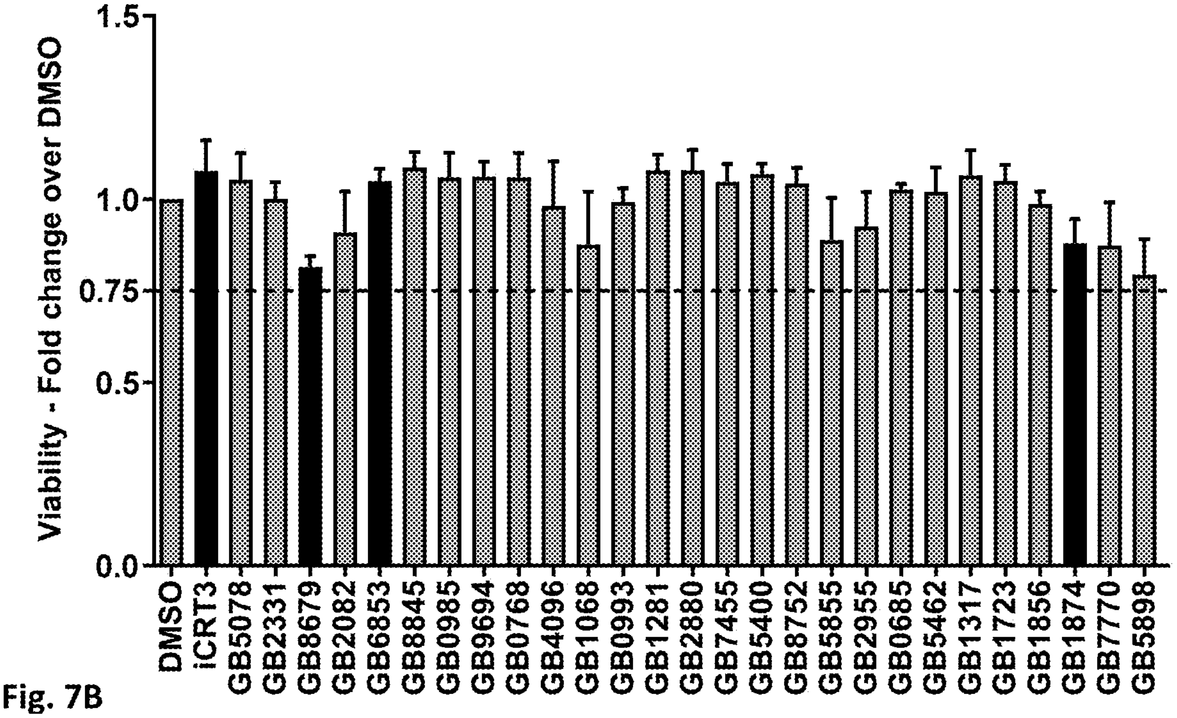
Figure 7B:
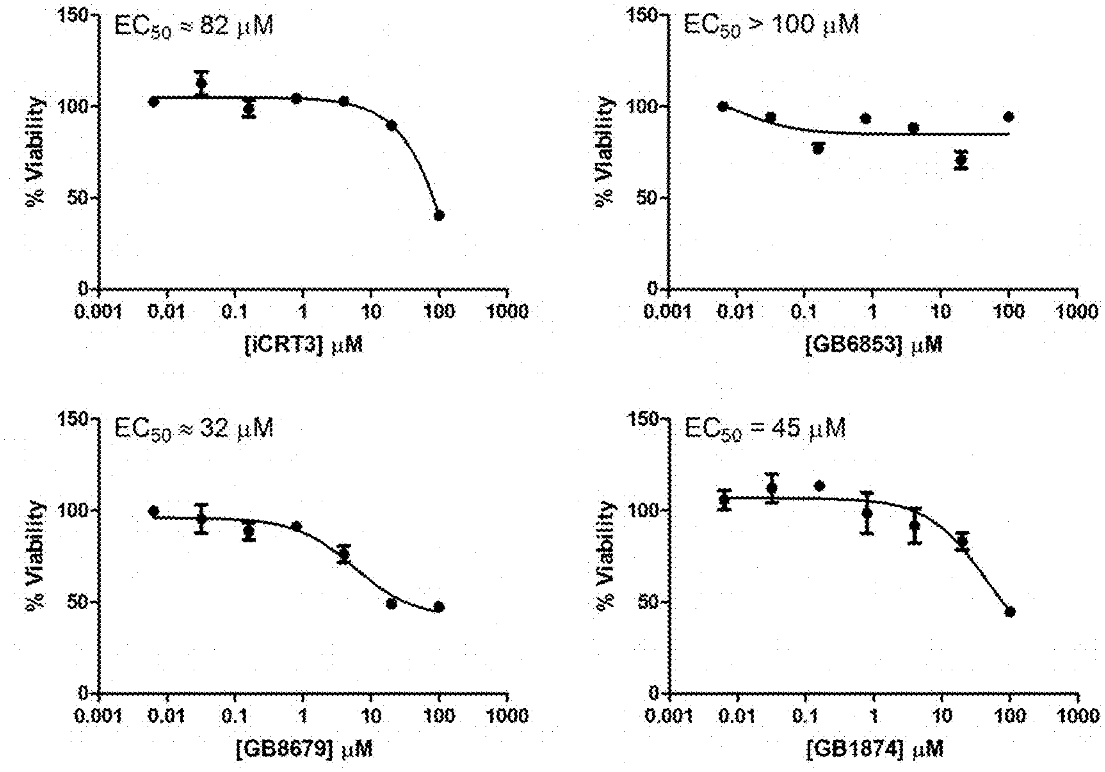

FIG. 7 depicts (FIG. 7A) cell viabilities of STF cells after 24 hr of compound treatment. The viability measurements of compound-treated cells were normalized to DMSO treated cells. Error bars represent standard deviation of 4 replicates. (FIG. 7B) Dose response effects of iCRT3 and hit compounds on the viability of STF cells after 24 hr treatment. The viability measurements of cells treated with compounds were normalized to DMSO treated cells. $IC_{50}$ values were calculated using a four-parameter nonlinear regression. Error bars represent standard deviation of 3 replicates.

Figure 8A:
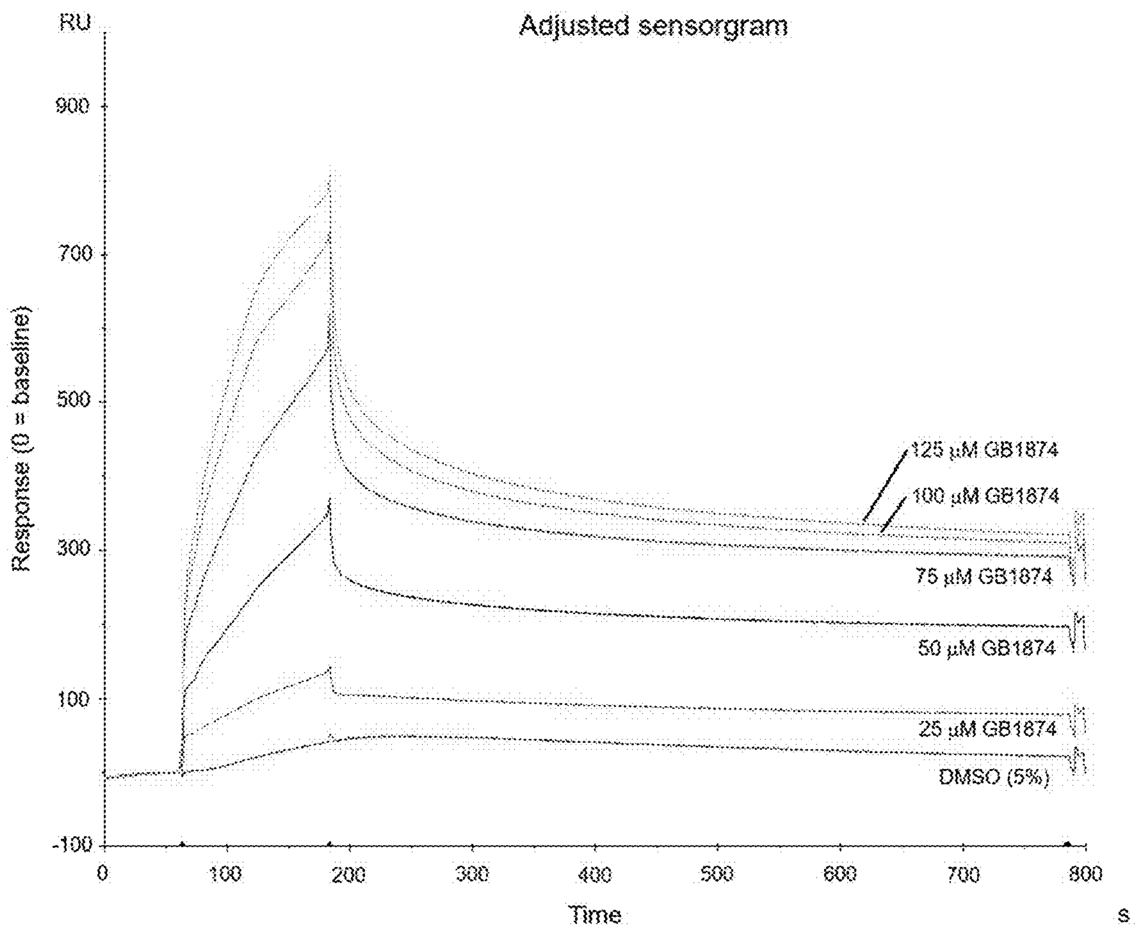
Figure 8B:
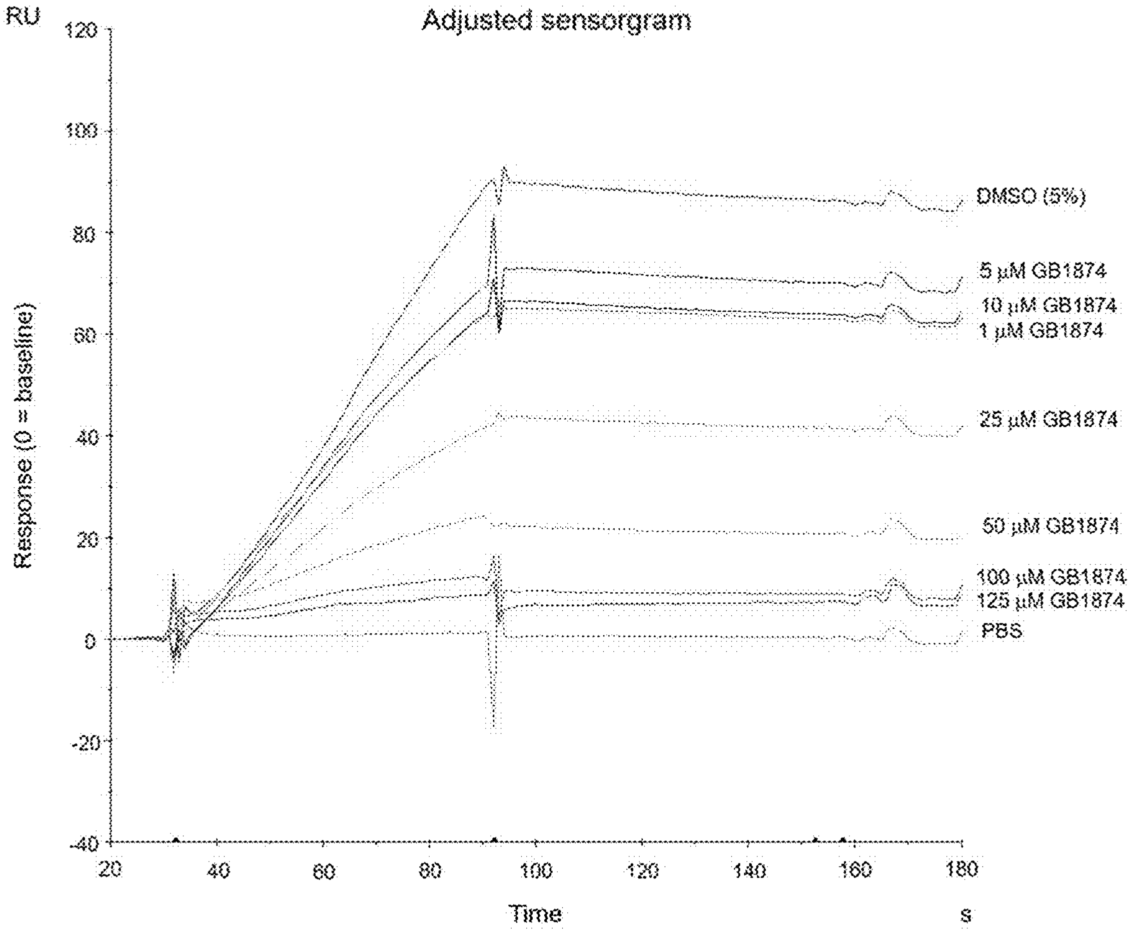

FIG. 8 depicts (FIG. 8A) Binding sensorgrams of different concentrations of analyte compound GB1874 to β-catenin ligand. (FIG. 8B) Binding sensorgrams of 50 nM β-catenin analyte to GST-TCF4 ligand. β-catenin was pre-incubated with different concentrations of compound GB1874 for 15 min prior to binding to GST-TCF4.

Figure 9A:
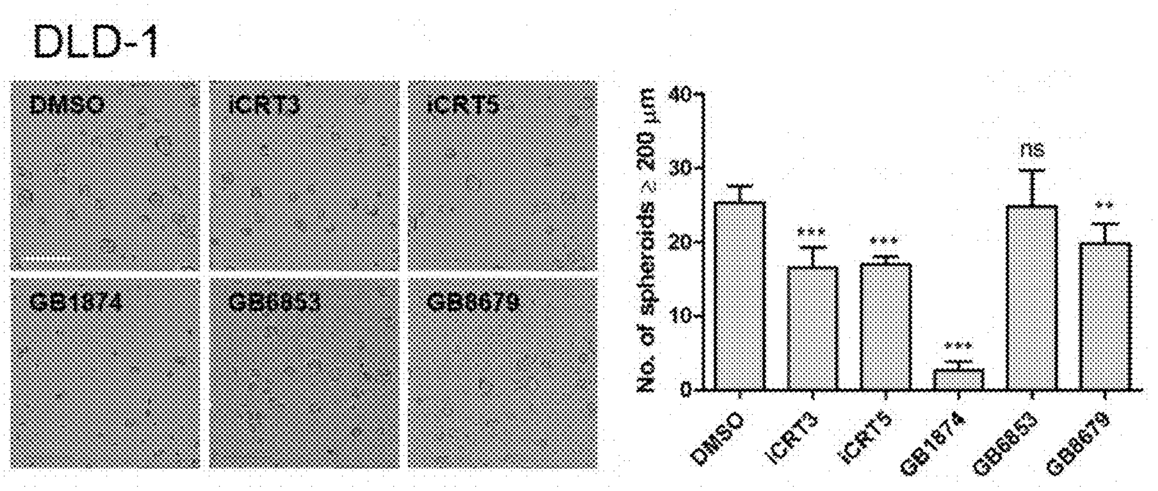
Figure 9B:
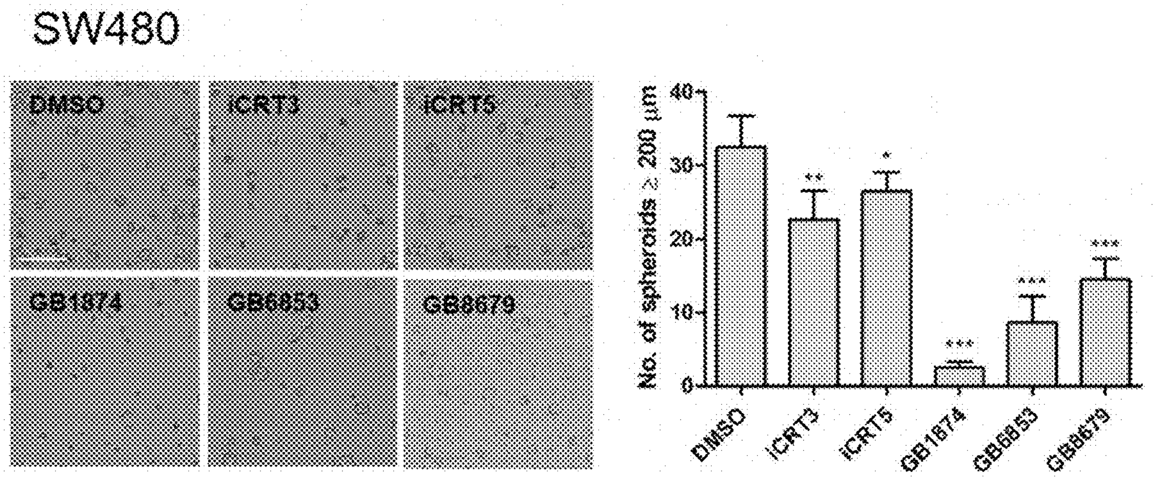
Figure 9C:
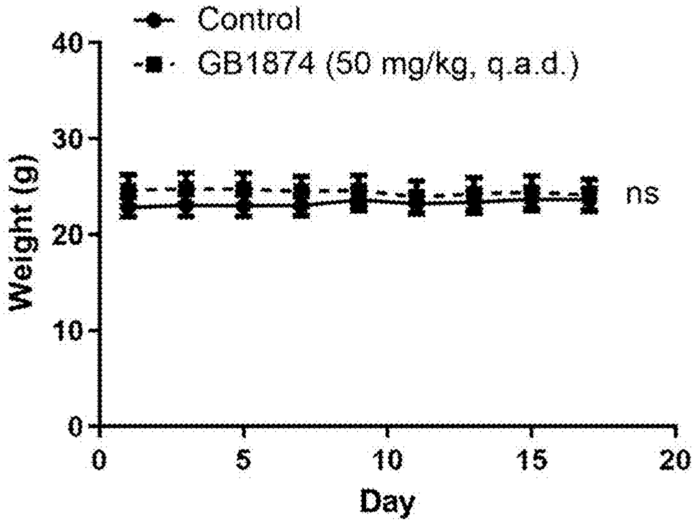

FIG. 9 depicts Effects of hit compounds on spheroid formation of (FIG. 9A) DLD-1 and (FIG. 9B) SW480 cells. The cells were grown in ultra-low attachment 96-well plates and treated with either DMSO or the compounds at 30 UM for 7 days, following which the number of spheroids ≥200 μm in size was determined. Two-tailed Student's t-test was carried out between compound treatment and DMSO control. *P<0.001, P<0.01, *P<0.05. Scale bar represents 1 mm. (FIG. 9C) NSG mice xenografted with HCT116 cells were treated with vehicle control (n=6) or 50 mg/kg GB1874 (n=6) via i.p. every other day for 2 weeks. Mice body weights were monitored over time. Two-tailed Student's t-test was carried out between control and treatment at day 17. ns P>0.05.

Figure 10:
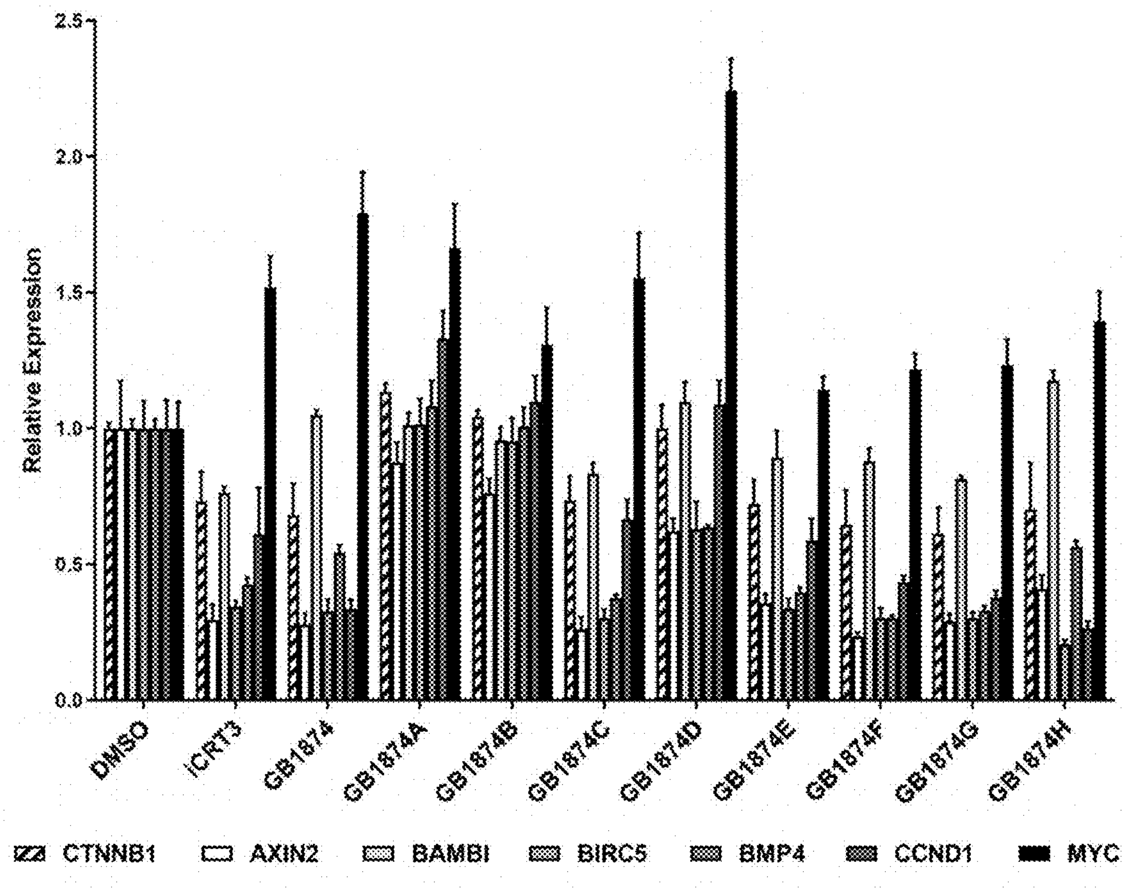

FIG. 10 depicts the effects of GB1874 and its analogues on the expression of beta-catenin (CTNNB1) and Wnt target genes.

Figure 11A:
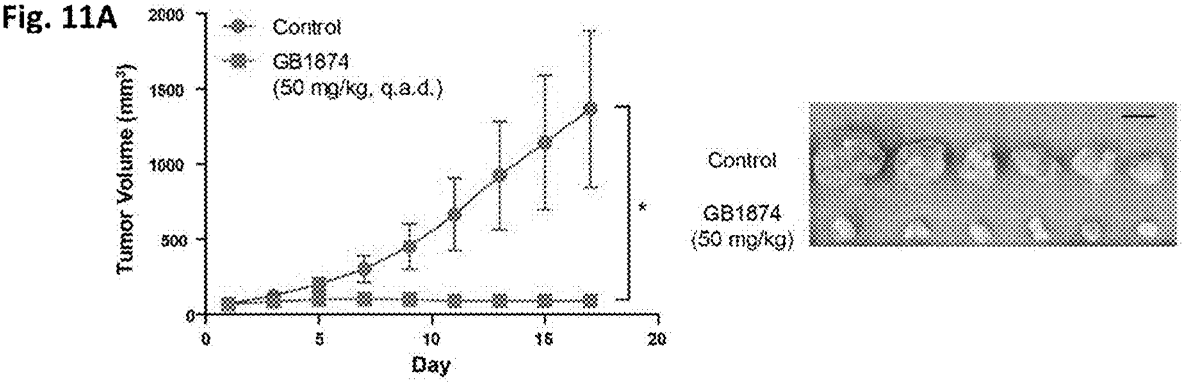
Figure 11B:
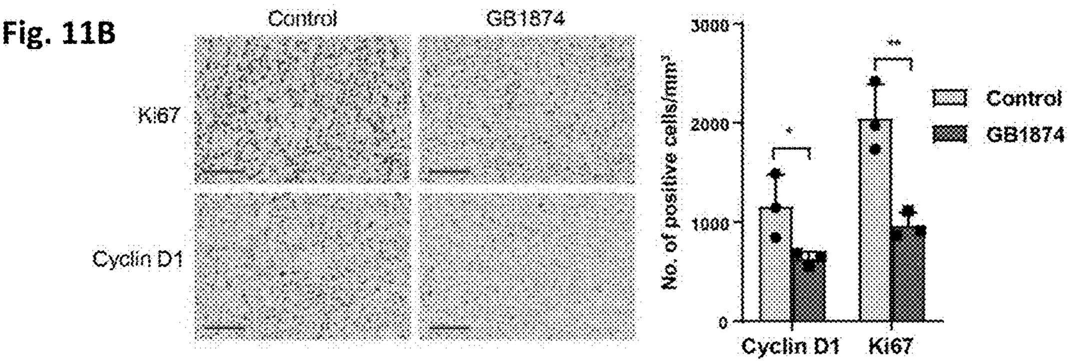

FIG. 11 depicts GB1874 inhibited growth of Wnt driven cells in vivo via inhibition of Wnt signalling. (FIG. 11A) NSG mice xenografted with HCT116 cells were treated with vehicle control (n=6) or 50 mg/kg GB1874 (n=6) via i.p. every other day for 2 weeks. Tumour volumes (left panel) were monitored over time. Two-way ANOVA was carried out between vehicle control and treatment tumour volumes. *P<0.05. Error bars represent mean±SEM. Images of tumours at the end of treatment are shown in the right panel. Scale bar represents 1 cm. (FIG. 11B) Representative IHC staining of tumours for Ki67 and cyclin D1 expression (left panel). Scale bar represents 100 μm. Quantification of the number of cyclin D1 and Ki67 expressing cells per unit tumour area (right panel). One-tailed Student's t test was carried out between vehicle control and treatment for each marker. **P<0.01, *P<0.05, ns P>0.05. Error bars represent mean±SD of 3 tumours.

DETAILED DESCRIPTION

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

In the context of this specification, the term "amino acid" is defined as having at least one primary, secondary, tertiary or quaternary amino group, and at least one acid group, wherein the acid group may be a carboxylic, sulfonic, or phosphonic acid, or mixtures thereof. The amino groups may be "alpha", "beta", "gamma" . . . to "omega" with respect to the acid group(s). The backbone of the "amino acid" may be substituted with one or more groups selected from halogen, hydroxy, guanido, heterocyclic groups. Thus term "amino acids" also includes within its scope glycine, alanine, valine, leucine, isoleucine, methionine, proline, phenylalanine, tryptophan, serine, threonine, cysteine, tyrosine, asparagine, glutamate, aspartate, glutamine, lysine, arginine and histidine, taurine, betaine, N-methylalanine etc. (L) and (D) forms of amino acids are included in the scope of this invention.

As used herein, the term "alkyl group" includes within its meaning monovalent ("alkyl") and divalent ("alkylene") straight chain or branched chain saturated aliphatic groups having from 1 to 10 carbon atoms, e.g., 1, 2, 3, 4, 5, 6, 7, 8, 9, or 10 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like.

The term "alkenyl group" includes within its meaning monovalent ("alkenyl") and divalent ("alkenylene") straight or branched chain unsaturated aliphatic hydrocarbon groups having from 2 to 10 carbon atoms, e.g., 2, 3, 4, 5, 6, 7, 8, 9, or 10 carbon atoms and having at least one double bond, of either E, Z, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 1-nonenyl, 1-decenyl, and the like.

The term "alkynyl group" as used herein includes within its meaning monovalent ("alkynyl") and divalent ("alkynylene") straight or branched chain unsaturated aliphatic hydrocarbon groups having from 2 to 10 carbon atoms and having at least one triple bond anywhere in the carbon chain. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, methylpentynyl, 1-heptynyl, 2-heptynyl, 1-octynyl, 2-octynyl, 1-nonyl, 1-decynyl, and the like.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In certain embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In certain embodiments, aryl groups can be optionally substituted. In certain embodiments, an aryl group is substituted with another aryl group and can be referred to as a biaryl group. Each of the aryl groups in the biaryl group can be optionally substituted.

As used herein, "heteroaryl" refers to an aromatic monocyclic ring system containing at least one ring heteroatom selected from oxygen (O), nitrogen (N), sulphur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkylxarylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In certain embodiments, heteroaryl groups can be optionally substituted.

The term "cycloalkyl" as used herein refers to cyclic saturated aliphatic groups and includes within its meaning monovalent ("cycloalkyl"), and divalent ("cycloalkylene"), saturated, monocyclic, bicyclic, polycyclic or fused polycyclic hydrocarbon radicals having from 3 to 10 carbon atoms, e.g., 3, 4, 5, 6, 7, 8, 9, or 10 carbon atoms. Examples of cycloalkyl groups include but are not limited to cyclopropyl, 2-methylcyclopropyl, cyclobutyl, cyclopentyl, 2-methylcyclopentyl, 3-methylcyclopentyl, cyclohexyl, and the like, The term "cycloalkenyl" as used herein, refers to cyclic unsaturated aliphatic groups and includes within its meaning monovalent ("cycloalkenyl") and divalent ("cycloalkenylene"), monocyclic, bicyclic, polycyclic or fused polycyclic hydrocarbon radicals having from 3 to 10 carbon atoms and having at least one double bond, of either E, Z, cis or trans stereochemistry where applicable, anywhere in the alkyl chain. Examples of cycloalkenyl groups include but are not limited to cyclopropenyl, cyclopentenyl, cyclohexenyl, and the like.

The term "heterocycloalkyl" as used herein, includes within its meaning monovalent ("heterocycloalkyl") and divalent ("heterocycloalkylene"), saturated, monocyclic, bicyclic, polycyclic or fused hydrocarbon radicals having from 3 to 10 ring atoms wherein 1 to 5 ring atoms are heteroatoms selected from O, N, NH, or S. Examples include pyrrolidinyl, piperidinyl, quinuclidinyl, azetidinyl, morpholinyl, tetrahydrothiophenyl, tetrahydrofuranyl, tetrahydropyranyl, and the like.

The term "heterocycloalkenyl" as used herein, includes within its meaning monovalent ("heterocycloalkenyl") and divalent ("heterocycloalkenylene"), saturated, monocyclic, bicyclic, polycyclic or fused polycyclic hydrocarbon radicals having from 3 to 10 ring atoms and having at least 1 double bond, wherein from 1 to 5 ring atoms are heteroatoms selected from O, N, NH or S.

The term "heteroaromatic group" and variants such as "heteroaryl" or "heteroarylene" as used herein, includes within its meaning monovalent ("heteroaryl") and divalent ("heteroarylene"), single, polynuclear, conjugated and fused aromatic radicals having 6 to 20 atoms wherein 1 to 6 atoms are heteroatoms selected from O, N, NH and S. Examples of such groups include pyridyl, 2,2'-bipyridyl, phenanthrolinyl, quinolinyl, thiophenyl, and the like.

The term "halogen" or variants such as "halide" or "halo" as used herein refers to fluorine, chlorine, bromine and iodine.

The term "heteroatom" or variants such as "hetero-" as used herein refers to O, N, NH and S.

The term "alkoxy" as used herein refers to straight chain or branched alkyloxy groups. Examples include methoxy, ethoxy, n-propoxy, isopropoxy, tert-butoxy, and the like.

The term "amino" as used herein refers to groups of the form $—NR_aR_b$ wherein $R_a$ and $R_b$ are individually selected from the group including but not limited to hydrogen, optionally substituted alkyl, optionally substituted alkenyl, optionally substituted alkynyl, and optionally substituted aryl groups.

The term "aromatic group", or variants such as "aryl" or "arylene" as used herein refers to monovalent ("aryl") and divalent ("arylene") single, polynuclear, conjugated and fused residues of aromatic hydrocarbons having from 6 to 10 carbon atoms. Examples of such groups include phenyl, biphenyl, naphthyl, phenanthrenyl, and the like.

The term "aralkyl" as used herein, includes within its meaning monovalent ("aryl") and divalent ("arylene"), single, polynuclear, conjugated and fused aromatic hydrocarbon radicals attached to divalent, saturated, straight and branched chain alkylene radicals.

The term "heteroaralkyl" as used herein, includes within its meaning monovalent ("heteroaryl") and divalent ("heteroarylene"), single, polynuclear, conjugated and fused aromatic hydrocarbon radicals attached to divalent saturated, straight and branched chain alkylene radicals.

The term "optionally substituted" as used herein means the group to which this term refers may be unsubstituted, or may be substituted with one or more groups independently selected from alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups, such as phosphono and phosphinyl, aryl, heteroaryl, alkylaryl, alkylheteroaryl, cyano, cyanate, isocyanate, —C(O)NH(alkyl), and $—C(O)N(alkyl)_2$.

The present invention includes within its scope all isomeric forms of the compounds disclosed herein, including all diastereomeric isomers, racemates and enantiomers. Thus, formulae (I) and (II) should be understood to include, for example, E, Z, cis, trans, (R), (S), (L), (D), (+), and/or (−) forms of the compounds, as appropriate in each case.

In the context of this invention the term "administering" and variations of that term including "administer" and "administration", includes contacting, applying, delivering or providing a compound or composition of the invention to an organism, or a surface by any appropriate means.

The term "subject" as used herein, refers to an animal, typically a mammal or a human, that will be or has been the object of treatment, observation, and/or experiment. When the term is used in conjunction with administration of a compound or drug, then the subject has been the object of treatment, observation, and/or administration of the compound or drug. In the context of this specification, the term "subject" includes humans and individuals of any species of social, economic or research importance including, but not limited to, members of the genus ovine, bovine, equine, porcine, feline, canine, primates (including human and non-human primates), rodents, murine, caprine, leporine, and avian. In certain embodiments, the subject is a human. In certain embodiments, the term "subject" can refer to a cell sample, tissue sample or organ sample derived a subject, including, for example, cultured cell lines, biopsy, blood sample, or fluid sample containing a cell.

The term "substituted" is intended to indicate that one or more (e.g., 1, 2, 3, 4, or 5; in some embodiments 1, 2, or 3; and in other embodiments 1 or 2) hydrogen atoms on the group indicated in the expression using "substituted" is replaced with a selection from the indicated organic or inorganic group(s), or with a suitable organic or inorganic group known to those of skill in the art, provided that the indicated atom's normal valency is not exceeded, and that the substitution results in a stable compound. Suitable indicated organic or inorganic groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, alkylsilyl, and cyano. Additionally, the suitable indicated groups can include, e.g., —X, —R, —O—, —OR, —SR, —S—, $—NR_2$, $—NR_3$, =NR, $—CX_3$, —CN, —OCN, —SCN, —N=C=O, —NCS, —NO, $—NO_2$, $=N_2$, $—N_3$, —NRC(=O)R, —C(=O)R, $—C(=O)NR_2$, $—S(=O)_2O—$, $—S(=O)_2R$, $—OS(=O)_2OR$, $—S(=O)_2NR_2$, $—OP(=O)(OR)_2$, $—P(=O)(OR)_2$, —C(=O)R, —C(=O)X, —C(S)R, —C(=O)OR, —C(=O)O—, —C(=S)OR, —C(=O)SR, —C(=S)SR, $—C(=O)NR_2$, $—C(=S)NR_2$, $—C(=NR)NR_2$, where each X is independently a halogen (or "halo" group): F, Cl, Br, or I; and each R is independently H, alkyl, aryl, heterocycle, protecting group or prodrug moiety. As would be readily understood by one skilled in the art, when a substituent is keto (i.e., =O) or thioxo (i.e., =S), or the like, then two hydrogen atoms on the substituted atom are replaced with the substituent.

In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the term "therapeutically effective amount" includes within its meaning a sufficient amount of a compound or composition of the invention to provide the desired therapeutic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

The present disclosure provides a compound useful for inhibiting β-cat or disrupting the interaction of β-cat and TCF4, wherein the compound has Formula 1:

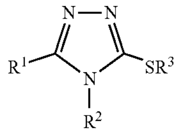

1 or a pharmaceutically acceptable salt thereof, wherein $R^1$ is —$(CR^4{}_2)_m$$XR^5$;

$R^2$ is alkyl, alkenyl, alkynyl, cycloalkyl, cycloalkenyl, heterocycloalkyl, heterocycloalkenyl, aryl, aralkyl, heteroaralkyl, or heteroaryl;

$R^3$ is —$(CR^6{}_2)_n$$R^7$;

$R^4$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl; or two instances of $R^4$ taken together with the carbon or carbons to which they are attached form a 3-7 membered cycloalkyl;

$R^5$ is hydrogen, cycloalkyl, cycloalkenyl, heterocycloalkyl, heterocycloalkenyl, aryl, or heteroaryl;

$R^6$ for each occurrence is independently selected from the group consisting of hydrogen, alkyl, alkenyl, alkynyl, cycloalkyl, cycloalkenyl, heterocycloalkyl, heterocycloalkenyl, aryl, heteroaryl, aralkyl, and heteroaralkyl; or two instances of $R^6$ taken together with the carbon or carbons to which they are attached form a 3-7 membered cycloalkyl;

$R^7$ is —(C═O)$R^8$, —(C═O)$OR^8$, or —(C═O)$N(R^8)_2$; or $R^7$ is a moiety having the Formula 2:

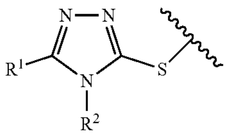

2

$R^8$ for each occurrence is independently selected from the group consisting of alkyl, alkenyl, alkynyl, cycloalkyl, cycloalkenyl, heterocycloalkyl, heterocycloalkenyl, aryl, heteroaryl, aralkyl, and heteroaralkyl; or two $R^8$ taken together with the nitrogen to which they are attached form a 3-7 membered heterocycloalkyl; or $R^6$ and $R^8$ taken together with the atoms to which they are attached form a 4-7 membered optionally substituted cycloalkyl or a 4-7 membered optionally substituted heterocycloalkyl;

m is a whole number selected from 0-4;

n is a whole number selected from 0-4; and

X is —O—, —S—, or is absent.

In certain embodiments, the compound of Formula I does not include the compound:

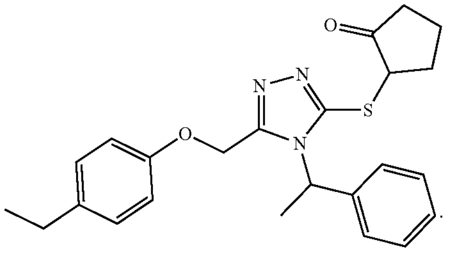 [SMILES: CCc1ccc(OCc2nnc(SC3CCCC3=O)n2C(C)c2ccccc2)cc1]

In certain embodiments, X is —O—, —S—, or is absent. In instances in which X is absent, $R^1$ can have the structure: —$(CR^4{}_2)_m$$R^5$, wherein m, $R^4$, and $R^5$ are as defined in any embodiment(s) described herein.

In certain embodiments, m is 0-3, 0-2, 0-1, or 1-2. In certain embodiments, X is O or S; and m is 1. In certain embodiments, X is absent and m is 1 or 2.

In certain embodiments, m is 0-3, 0-2, 0-1, or 1-2.

In certain embodiments, n is 0-3, 0-2, 0-1, or 1-2.

In certain embodiments, $R^2$ is alkyl, aralkyl, heteroaralkyl; or —$(CR^9{}_2)_p$$R^{10}$, wherein p is a whole number selected from 0-4; $R^9$ for each occurrence is independently hydrogen or alkyl; and $R^{10}$ is alkenyl, alkynyl, cycloalkyl, cycloalkenyl, heterocycloalkyl, heterocycloalkenyl, aryl, heteroaryl, aralkyl, or heteroaralkyl. In certain embodiments, $R^{10}$ is an optionally substituted phenyl, an optionally substituted furan, an optionally substituted thiophene, an optionally substituted pyrrole, an optionally substituted immidazole, an optionally substituted oxazole, an optionally substituted isoxazole, an optionally substituted thiazole, an optionally substituted pyridine, an optionally substituted pyrazine, or an optionally substituted triazine.

In instances in which $R^2$ is —$(CR^9{}_2)_n$$R^{10}$, P can be 0-3, 0-2, 0-1, or 1-2. In certain embodiments, $R^9$ for each occurrence is independently hydrogen or alkyl. In certain embodiments, $R^2$ is —$(CH_2)R^{10}$ or —$(CHMe)R^{10}$; and $R^{10}$ is as defined herein.

In certain embodiments, $R^4$ for each occurrence is hydrogen or alkyl; or two instances of $R^4$ taken together with the carbon or carbons to which they are attached form a 3-7 or 3-6 membered cycloalkyl. In certain embodiments, $R^4$ is hydrogen.

In certain embodiments, $R^5$ is cycloalkyl, cycloalkenyl, heterocycloalkyl, heterocycloalkenyl, aryl, or heteroaryl. In certain embodiments, $R^5$ is aryl, or heteroaryl. In certain embodiments, $R^5$ is an optionally substituted phenyl.

In certain embodiments, $R^7$ is —(C═O)$R^8$, —(C═O)$OR^8$, or —(C═O)$N(R^8)_2$, wherein $R^8$ is alkyl, cycloalkyl, aryl; or two $R^8$ taken together with the nitrogen to which they are attached form a 3-7 membered heterocycloalkyl; or $R^6$ and $R^8$ taken together with the atoms to which they are attached form a 4-7 membered optionally substituted cycloalkyl or a 4-7 membered optionally substituted heterocycloalkyl.

In instances in which two $R^8$ taken together with the nitrogen to which they are attached form a 3-7 membered heterocycloalkyl, the 3-7 membered heterocycloalkyl can contain 1 or 2 heteroatoms selected from oxygen, sulphur, and nitrogen in its ring system.

In instances in which $R^6$ and $R^8$ taken together with the atoms to which they are attached form a 4-7 membered optionally substituted heterocycloalkyl, the compound can have Formula 5:

5

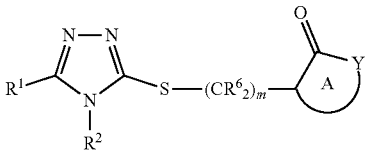

or a pharmaceutically acceptable salt thereof, wherein each of $R^1$, $R^2$, $R^6$, and $R^8$ is independently as defined herein; m is 0-4; and A represents a 4-7 membered optionally substituted cycloalkyl or a 4-7 membered optionally substituted heterocycloalkyl containing 1 or 2 heteroatoms selected from oxygen, sulphur, and nitrogen in its ring system; and Y is —O—, —N($R^8$)—, or absent; or the compound can have Formula 6:

6

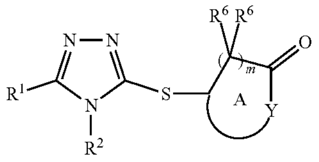

or a pharmaceutically acceptable salt thereof, wherein each of $R^1$, $R^2$, $R^6$, and $R^8$ is independently as defined herein; m is 0-3; and A represents a 4-7 membered optionally substituted cycloalkyl or a 4-7 membered optionally substituted heterocycloalkyl containing 1 or 2 heteroatoms selected from oxygen, sulphur, and nitrogen in its ring system; and Y is —O—, —N($R^8$)—, or absent.

In certain embodiments, $R^8$ is $C_1$-$C_{10}$ alkyl, $C_3$-$C_7$ cycloalkyl, biaryl, or a polycyclic hydrocarbon; or two $R^8$ taken together with the nitrogen to which they are attached form a 3-7, 4-7, 5-7, or 5-6 membered optionally substituted heterocycloalkyl; or the compound has Formula 6, wherein A is a 5-6 membered optionally substituted cycloalkyl.

In instances in which $R^7$ is a moiety having Formula 2, the compound can be represented by the Formula 7:

7

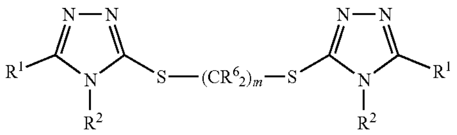

or a pharmaceutically acceptable salt thereof, wherein each $R^1$, $R^2$, $R^6$, and m are each independently as defined herein.

In certain embodiments, the compound has Formula 3:

3

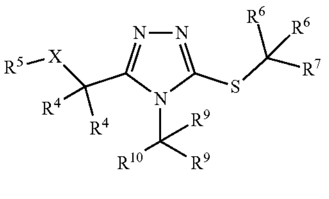

or a pharmaceutically acceptable salt thereof, wherein $R^4$ for each occurrence is independently selected from the group consisting of hydrogen and alkyl;

$R^5$ is aryl or heteroaryl;

$R^6$ for each occurrence is independently selected from the group consisting of hydrogen and alkyl;

$R^7$ is —(C═O)$R^8$, —(C═O)O$R^8$, or —(C═O)N($R^8$)$_2$; or $R^7$ is a moiety having Formula 4:

4

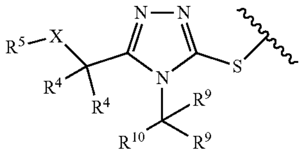

$R^8$ for each occurrence is independently selected from the group consisting of alkyl, cycloalkyl, and aryl; or two instances of $R^8$ taken together with the nitrogen to which they are attached form a 5-6 membered heterocycloalkyl; or $R^6$ and $R^8$ taken together with the atoms to which they are attached form a 5-6 membered cycloalkyl;

$R^9$ for each occurrence is independently selected from the group consisting of hydrogen and alkyl;

$R^{10}$ is cycloalkyl, aryl or heteroaryl; and

X is —O— or absent.

In certain embodiments, the compound has Formula 3, wherein $R^4$ is hydrogen; $R^5$ is aryl; $R^9$ for each occurrence is independently selected from the group consisting of hydrogen and alkyl; $R^{10}$ is aryl; $R^6$ for each occurrence is independently selected from the group consisting of hydrogen and alkyl; and $R^7$ is —(C═O)O$R^8$ or —(C═O)N($R^8$)$_2$, wherein $R^8$ for each occurrence is independently selected from the group consisting of alkyl, cycloalkyl, and aryl; or two instances of $R^8$ taken together with the nitrogen to which they are attached form a 5-6 membered heterocycloalkyl.

In certain embodiments, the compound has Formula 8:

8

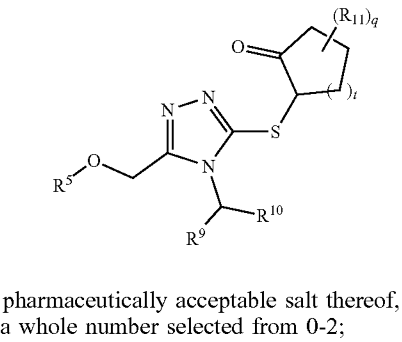

or a pharmaceutically acceptable salt thereof, wherein q is a whole number selected from 0-2;

t is 1 or 2;

$R^5$ is optionally substituted phenyl;

$R^9$ is hydrogen or alkyl;

$R^{10}$ is optionally substituted phenyl;

$R^{11}$ for each occurrence is independently selected from the group consisting of alkyl, alkenyl, alkynyl, cycloalkyl, cycloalkenyl, heterocycloalkyl, heterocycloalkenyl, aryl, heteroaryl, aralkyl, heteroaralkyl, —SR, —OR, —O(C═O)R, —O(C═O)OR, —O(C═O)N(R)$_2$, —N$R_2$, or —N(R)(C═O)N(R)$_2$, wherein R for each occurrence is independently hydrogen, alkyl, aryl, or heteroaryl; or two R taken together with the nitrogen or nitrogens that they are attached form a 3-7 membered heterocycloalkyl.

In certain embodiments, the compound has Formula 8, q is 0 or 1; t is 1; $R^9$ is hydrogen or $C_1$-$C_3$ alkyl; and $R^{11}$ is alkyl, cycloalkyl, heterocycloalkyl, aryl, heteroaryl, aralkyl, or heteroaralkyl.

In certain embodiments, the compound is selected from the group consisting of:

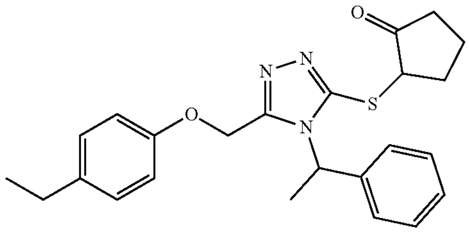

,

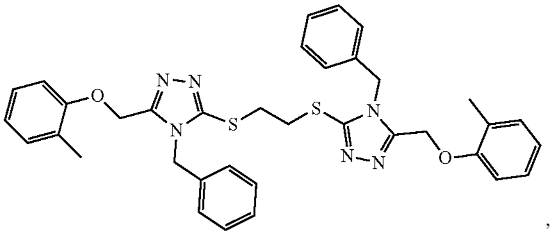

,

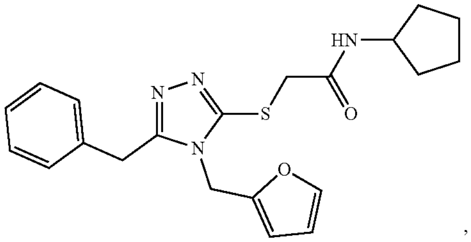

,

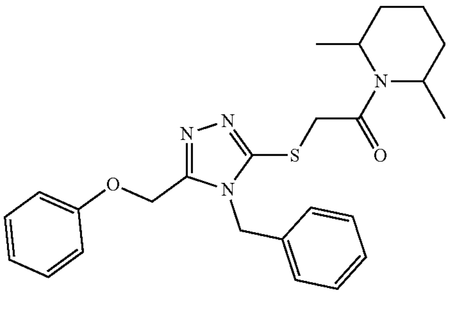

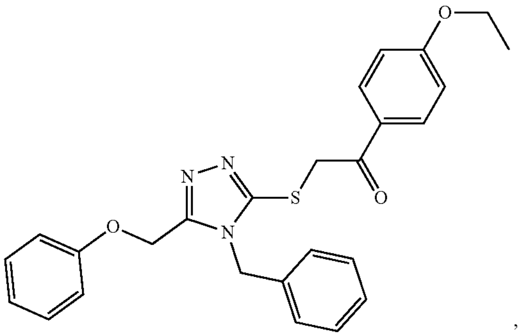

,

-continued

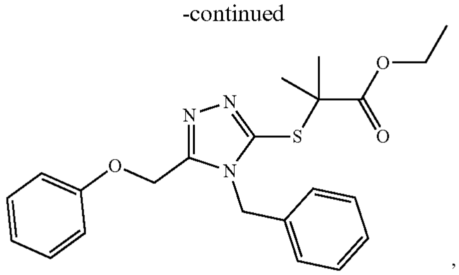

,

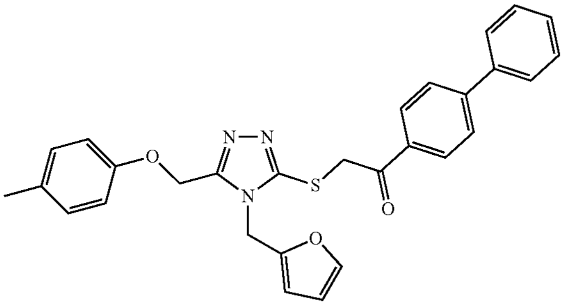

,

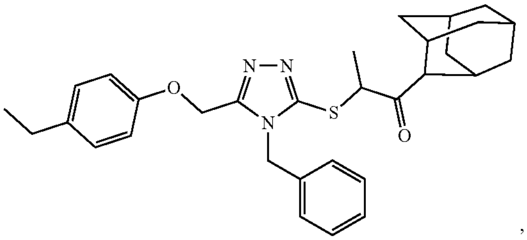

, and

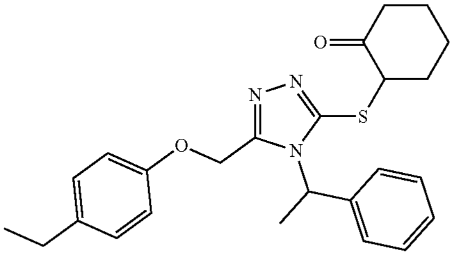

, or a pharmaceutically acceptable salt thereof.

The pharmaceutically acceptable salts of the compounds described herein can include the conventional nontoxic salts or quaternary ammonium salts of the compounds, e.g., from non-toxic organic or inorganic acids. For example, such conventional non-toxic salts include those derived from inorganic acids such as hydrochloride, hydrobromic, sulphuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds described herein may contain one or more acidic functional groups and, thus, are capable of forming pharmaceutically-acceptable salts with pharmaceutically-acceptable bases. The term "pharmaceutically-acceptable salts" in these instances can refer to the relatively non-toxic, inorganic and organic base addition salts of compounds described herein. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The inhibition of β-cat or disruption of the interaction of β-cat and TCF4 may be conducted in vitro, in vivo, or ex vivo.

The inhibition of β-cat or disruption of the interaction of β-cat and TCF4 may be conducted by contacting one or more of the compounds described herein with at least one of: β-cat and the β-cat-TCF4 complex.

Contacting β-cat or the β-cat/TCF4 complex with a compound of Formula 1 can result in one or more of: inhibition of β-cat function(s), inhibition of the interaction of β-cat and TCF4, and disruption of the β-cat/TCF4 complex and can further result in attenuation of the Wnt signalling.

Accordingly, the method for inhibiting β-cat or disrupting the interaction of β-cat and TCF4 can be used to treat diseases in which inhibition of β-cat, disruption of the β-cat/TCF4 complex, and/or attenuation of the Wnt signalling pathway results in the amelioration of a disease or health condition.

Disrupting the interaction between β-cat and TCF4 can refer to one or both of inhibiting the association of β-cat with TCF4 or inducing the disassociation of the β-cat-TCF4 complex thereby forming β-cat and TCF4.

The amount or concentration of the compound of Formula 1 required to be administered can be readily determined by a person of ordinary skill in the art using well known methods and the disclosure provided herein.

Provided herein is a method of treating a disease or health condition that is ameliorated by inhibiting the interaction between β-cat and TCF4 in a subject in need thereof, the method comprising administering a therapeutically effective amount of a compound described herein. In certain embodiments, the subject is a human.

The present disclosure also provides a compound as described herein for use in treating a disease or health condition that is ameliorated by inhibiting β-cat or disrupting the interaction between β-cat and TCF4.

The present disclosure further provides the use of a compound as described herein in the manufacture of a medicament for the treatment of a disease or health condition that is ameliorated by inhibiting β-cat or disrupting the interaction between β-cat and TCF4.

The disease or health condition can be cancer, neurodegenerative, a metabolic disease, a cardiovascular disease, fibrosis, or a bone disease.

In certain embodiments, the disease or health condition is a cancer characterized by aberrant activation of one or more of the Wnt, Myc and Hippo signalling pathways.

In certain embodiments the disease or health condition is a cancer characterized by aberrant activation of Wnt/β-cat signalling pathway.

Aberrant Wnt/β-cat pathway signalling has been implicated in a number of different cancers and a number of genetic defects in this pathway may contribute to tumour promotion and progression.[1] Activation of the Wnt/β-cat pathway is one of the most frequent signalling abnormalities in several human cancers, such as colorectal carcinomas,[2] melanomas,[3] hepatoblastomas,[4] medulloblastomas,[5] prostatic carcinomas,[6] and uterine and ovarian endometrioid adenocarcinomas.[7-10] Wnt/β-catenin pathway activation is also common in metaplastic carcinomas of the breast.[11]

Accordingly, the methods provided can be used in the treatment of a cancer selected from the group consisting of colorectal cancer, hepatocellular carcinoma, melanoma, liver cancer, breast cancer, prostate cancer, leukemia, thyroid cancer, brain cancer, medulloblastoma, hepatoblastoma, desmoid tumor, osteoma, head and neck cancer, uterine and ovarian endometrioid adenocarcinoma.

In certain embodiments, the cancer is colorectal cancer characterized by aberrant activation of Wnt/β-cat signalling pathway.

EXAMPLES

Generation of Virtual Chemical Libraries

The training library is composed of three known inhibitors of β-cat-TCF4 complex including iCRT3, iCRT5 and iCRT14,[12] and 150 property-matching computational decoys selected from ZINC database[13] by the DUD-E approach[14] as negative controls. The validation library is composed of 63 iCRT3 analogues synthesized in the DasGupta lab. The virtual screening library is composed of 10240 compounds that were purchased from Enamine (https://enamine.net/).

Molecular Docking Screens

Spheres and grids were generated prior to docking. 45 matching spheres serving to orient database compounds in the site were generated by augmenting the ligand-derived spheres with the receptor-derived spheres. The ligand-derived spheres were represented by the positions of non-hydrogen atoms of the crystal structures of TCF4 peptide fragments at the beginning and replaced by docked poses of iCRT ligands in the following rounds. The receptor-derived spheres were calculated using the program SPHGEN[15] from the molecular surface of the binding site. Docking screens was performed with DOCK version 3.6.[16] The docked compounds were ranked by the docking energy that is the sum of van der Waals, Poisson-Boltzmann electrostatic, and ligand desolvation penalty terms.

Docking Performance Evaluation

The accuracy of the structural models in ligand prediction was evaluated by the enrichment for the known ligands among the top scoring compounds, measured by the early enrichment factor EF1 and the overall enrichment log AUC which is analogous to the area under the curve (AUC) of the receiver operating characteristic (ROC) but gives early enrichment more weight.[16,17]

Cell Lines

Wnt STF reporter cells (HEK 293 cells stably transfected with TOPFlash reporter) and STF3A reporter cells (STF cells with constitutive secretion of Wnt3A) were kind gifts from David Virshup (Duke-NUS Graduate Medical School, Singapore). HCT116, DLD-1, and SW480 cell lines were obtained from ATCC. The Hippo pathway TEAD reporter (cat. #60618) and Myc signalling pathway reporter (cat. #60520) cells lines were purchased from BPS Bioscience, Inc.

Culture Media

STF, STF3A, and DLD-1 cells were cultured in Dulbecco's modified eagle medium (DMEM, Gibco cat. #11965084) supplemented with 10% fetal bovine serum (FBS, Hyclone cat. #SV30160.03) and 100 U/mL penicillin-streptomycin (Gibco cat. #15140122). HCT116, SW480, and Myc signalling pathway reporter cells were cultured in McCoy's 5A medium (Gibco cat. #16600108) supplemented with 10% FBS and 100 U/mL penicillin-streptomycin. The medium for Myc signalling pathway reporter cells was additionally supplemented with 400 μg/mL G-418 sulfate (Gold Biotechnology cat. #G-418-5). Hippo pathway TEAD reporter cells were cultured in minimum essential medium (MEM) with Earle's balanced salts (EBSS) (Hyclone cat. #SH30024.01) supplemented with 10% FBS, 100 U/mL penicillin-streptomycin, 1% MEM non-essential amino acids (NEAA, Gibco cat. #11140050), 1 mM sodium pyruvate (Gibco cat. #11360070), 400 μg/mL G-418 sulfate, and 10 μg/mL Insulin (Sigma Aldrich cat. #I1882-100MG). The medium for spheroid formation was DMEM/F-12 (Gibco cat. #11320082) supplemented with B27 (Gibco cat. #12587010), 100 U/mL penicillin-streptomycin, 20 ng/mL EGF (Gibco cat. #PHG0313), 20 ng/mL bFGF (Gibco cat. #PHG0023), and 3% matrigel (Corning cat. #354234).

TOPFlash (Wnt Signalling) Reporter Screen

STF cells were seeded as 20,000 cells in 100 μL culture medium per well in 96-well plates (Corning cat. #3903 & 3904). The next day, candidate compounds in DMSO were added to the cells at a final concentration of 10 μM, 1% DMSO. The cells were also stimulated with Wnt3A conditioned medium. After 24 hr incubation, the viability of the cells were determined with PrestoBlue cell viability reagent (Invitrogen cat. #A13262) while the TOPFlash reporter activity was determined with Steady-Glo luciferase reagent (Promega cat. #E2550) according to the manufacturers' protocols.

Reporter Lines Dose Response

Wnt Signalling Reporter

The Wnt STF reporter cells were seeded as 20,000 cells in 100 μL culture medium per well in 96-well plates (Corning cat. #3903, Falcon cat. #353072). The next day, 5-fold dilutions of the compounds in DMSO were added to the cells at a final concentration of 1% DMSO. The cells were also stimulated with 500 ng/mL recombinant human Wnt3A (RnD systems, cat. #5036-WN-010). After 24 hr incubation, the viability of the cells was determined with cell counting kit-8 (CCK-8, Dojindo cat. #CK04) cell viability reagent according to the manufacturer's protocol while the TOPFlash reporter activity was determined with Steady-Glo luciferase reagent.

The Wnt STF3A reporter cells were seeded as 20,000 cells in 100 μL culture medium per well in 96-well plates (Corning cat. #3903, Falcon cat. #353072). The next day, 5-fold dilutions of the compounds in DMSO were added to the cells at a final concentration of 1% DMSO. After 24 hr incubation, the viability of the cells was determined with cell counting kit-8 (CCK-8, Dojindo cat. #CK04) cell viability reagent according to the manufacturer's protocol while the TOPFlash reporter activity was determined with Steady-Glo luciferase reagent.

Myc Signalling Reporter

The Myc reporter (Luc)-HCT116 cells were seeded as 25,000 cells in 100 μL assay medium per well in 96-well plates (Corning cat. #3903, Falcon cat. #353072). The assay medium consists of the growth medium without G-418. The next day, 4-fold dilutions of the compounds in DMSO were added to the cells at a final concentration of 1% DMSO. After 24 hr incubation, the viability of the cells was determined with PrestoBlue cell viability reagent while the luciferase reporter activity was determined with Steady-Glo luciferase reagent.

Hippo Signalling Reporter

The Hippo TEAD reporter cells were seeded as 100,000 cells in 100 μL assay medium per well in 96-well plates (Corning cat. #3903, Falcon cat. #353072). The assay medium consists of the growth medium without G-418. The next day, 5-fold dilutions of the compounds in DMSO were added to the cells at a final concentration of 1% DMSO. After 24 hr incubation, the viability of the cells was determined with CCK-8 cell viability reagent while the luciferase reporter activity was determined with Steady-Glo luciferase reagent.

Dose Response Studies with CRC Cell Lines

HCT116, DLD-1, and SW480 cells were seeded as 5,000 cells in 100 μL growth medium per well in 96-well plates (Corning cat. #3903). The next day, 5-fold dilutions of the compounds in DMSO were added to the cells at a final concentration of 1% DMSO. After 24 hr incubation, the viability of the cells was determined with CellTiter-Glo luminescent cell viability reagent (Promega cat. #G7573) according to the manufacturer's protocol.

Data Analysis for Dose Response Studies

The average signal from DMSO treated wells was calculated for each plate, and the signal from each treatment well was normalized against the average DMSO signal from the respective plate. The normalized values were plotted against the concentrations tested using GraphPad Prism 5, and the $EC_{50}$ values were determined through either three- or four-parameter nonlinear regression.

Proliferation Assay

HCT 116 cells were seeded as 3,000 cells in 100 μL growth medium per well in 96-well plates (Corning cat. #3903) and allowed to attached overnight. Cells were then treated continuously with compounds at a final concentration of 10 μM, 0.1% DMSO, for 4 days with daily medium change. Cell proliferation each day was determined using CellTiter-Glo luminescent cell viability assay (Promega cat. #G7573) according to the manufacturer's protocol.

Spheroid Formation Assay

HCT116, DLD-1, and SW480 cells were seeded as 150 cells in 200 μL spheroid medium per well in 96-well ultra-low attachment plates (Corning cat. #3474). The compounds were added on the day of cell seeding at a final concentration of 30 μM, 0.5% DMSO. The cells were grown at 37° C., 5% $CO_2$ and images of the spheroids formed were taken on days 7 and 10 after cell seeding using the Operetta CLS system (Perkin Elmer).

Western Blotting

HCT116 cells were treated with compounds for 18 hr at a final concentration of 50 μM, 1% DMSO. Cells were lysed on ice in RIPA buffer (Thermo cat. #89900) containing cOmplete™ protease inhibitor cocktail (Roche cat. #11697498001) and PhosSTOP phosphatase inhibitor cocktail (Roche cat. #04906837001). 30 μg per sample of total cellular protein was resolved by SDS-PAGE and blotted onto PVDF membrane (Millipore cat. #IPVH00010). Primary antibodies were incubated overnight at 4° C. and the blots were detected with either IRDye 800CW goat anti-rabbit antibody (LI-COR cat. #926-32211) or IRDye 680RD goat anti-mouse antibody (LI-COR cat. #926-68070) at 1:5000 dilution. Signals were visualized with the LI-COR Odyssey CLx imaging system and bands were quantified using LI-COR Image Studio data analysis software. The primary antibodies used were Met (Cell Signalling Technology cat. #8198, 1:1000), cyclin D1 (Cell Signalling Technology cat. #2978, 1:1000), survivin (Santa Cruz cat. #sc-10811, 1:500), ECAD (Cell Signalling Technology cat. #3195, 1:1000), TCF4/TCF7L2 (Cell Signalling Technology cat. #2569, 1:1000), β-cat (Cell Signalling Technology cat. #8480, 1:1000), β-actin (Abcam cat. #ab8226, 1:3000).

Co-Immunoprecipitation

HCT116 cells were treated for 18 hr with compounds at the indicated concentrations. Cells were lysed on ice in lysis buffer containing 20 mM HEPES, pH 7.5, 137 mM NaCl, 1.5 mM $MgCl_2$, 1 mM EGTA, 1 mM dithiothreitol (DTT), 1% Triton X-100, 10% glycerol, cOmplete protease inhibitor cocktail (Roche cat. #11697498001), and 1 mM $Na_3VO_4$. Each sample of cleared protein lysate was incubated overnight at 4° C. with 4 μg anti-β-cat antibody (Sigma cat. #C7207) followed by 1 hr incubation with a 50 μL slurry of Dynabeads Protein G (Invitrogen cat. #10004D) at 4° C. The beads were then washed three times with lysis buffer at 4° C., and the bound protein was eluted by heating the beads with 30 μL (per sample) of SDS sample buffer at 95° C. for 7 min. protein was resolved by SDS-PAGE and blotted onto PVDF membrane (Millipore cat. #IPVH00010). Primary antibodies were incubated overnight at 4° C. and the blots were detected with either IRDye 800CW goat anti-rabbit antibody (LI-COR cat. #926-32211) or IRDye 680RD goat anti-mouse antibody (LI-COR cat. #926-68070) at 1:5000 dilution. Signals were visualized with the LI-COR Odyssey CLx imaging system and bands were quantified using LI-COR Image Studio data analysis software. The primary antibodies used were E-cadherin (Abcam cat. #ab15148, 1:1000), TCF4/TCF7L2 (Cell Signalling Technology cat. #2569, 1:1000), β-cat (Cell Signalling Technology cat. #8480, 1:1000).

Protein Expression and Purification

BL21(DE3) cells harboring pET-28 β-cat expression vector of His-tagged human β-cat (134-668) were cultured at 37° C. until $OD_{600}$=0.6-0.8. The cells were then induced with 500 μM isopropyl-β-D-thiogalactopyranoside (IPTG) for 6-8 hr at 23° C. Cells were lysed by sonication in lysis buffer containing 20 mM Tris (pH 8.8), 250 mM NaCl, 2 mM DTT, 5% glycerol, 0.1% Triton X-100, and cOmplete protease inhibitor cocktail (EDTA free, Roche cat. #11873580001). The lysate was incubated with Ni-NTA agarose beads (Qiagen cat. #30210) at 4° C. for 1 hr, and the beads were then washed with lysis buffer containing 20 mM imidazole. Bound protein was eluted with buffer containing 20 mM Tris (pH 8.8), 250 mM NaCl, 0.5 mM tris(2-carboxyethyl)phosphine (TCEP), 5% glycerol, and 250 mM imidazole.

GST-tagged TCF4 N-terminal domain was expressed similarly in BL21(DE3) cells, induced for 2-4 hr at 23° C. with IPTG, and purified from glutathione agarose beads (Pierce cat. #16100) using buffer containing 20 mM Tris (pH 8.8), 250 mM NaCl, 0.5 mM TCEP, 5% glycerol, and 10 mM reduced glutathione.

Surface Plasmon Resonance (SPR) Studies

Binding to β-Cat

Surface plasmon resonance experiments were performed using a BIACORE T100 (GE Healthcare) on a CM5 series S sensor chip (GE Healthcare cat. #BR-1005-30). His-tagged β-cat (60 kDa, >90% pure based on SDS-PAGE) was immobilized using amine-coupling chemistry. The surfaces of flow cells one and two were activated with a 1:1 mixture of 0.1 M NHS (N-hydroxysuccinimide) and 0.1 M EDC (3-(N,N-dimethylamino) propyl-N-ethylcarbodiimide) at a flow rate of 5 μL/min. The ligand at a concentration of 1 μM in PBS, pH 6.0, was immobilized at a density of 8000 RU on flow cell 2 and flow cell 1 was left blank to serve as a reference surface. Both surfaces were blocked with 1 M ethanolamine, pH 8.0. To collect binding data, compound GB1874 in PBS (pH 7.5) containing 5% DMSO, was injected over the two flow cells at concentrations of 125, 100, 80, 60, 40 and 20 μM at a flow rate of 30 μL/min and at a temperature of 25° C. The complex was allowed to associate and dissociate for 120 and 600 s, respectively. The surfaces were regenerated with a 30 s injection of 50 mM NaOH. The RU responses were collected and plotted against the concentration of GB1874 tested using GraphPad Prism 5. The dissociation constant $K_D$ was obtained through the nonlinear specific binding with Hill slope curve fitting function.

Inhibition of β-Cat-TCF4 Interaction

GST-tag TCF4 N-terminal domain (31 kDa, >90% pure based on SDS-PAGE) was immobilized on a CM5 series S sensor chip using amine-coupling chemistry. The ligand at a concentration of 0.5 μM in 10 mm citrate buffer, pH 4.0, was immobilized at a density of 400 RU on flow cell 4 and flow cell 3 was left blank to serve as a reference surface. For inhibition studies, 50 nM His-tagged β-cat was pre-incubated with different concentrations of compound GB1874 in PBS containing 5% DMSO for 15 min at room temperature. The mixture was injected over the two flow cells at a flow rate of 30 μL/min and at a temperature of 25° C. The complex was allowed to associate and dissociate for 60 s each and the surfaces were regenerated with a 30 s injection of 50 mM NaOH. The RU responses were collected and plotted against the concentration of GB1874 tested using GraphPad Prism 5. The inhibitory $IC_{50}$ value of compound GB1874 was obtained through a four-parameter nonlinear regression.

Mouse Xenograft and Compound Treatment

HCT 116 cells ($1\times10^6$ cells per site) and were implanted subcutaneously into the right flanks of 5-7 weeks old NSG (NOD scid gamma) (Jackson Laboratory, stock no. 005557) mice. When tumours reached a size of 60-100 $mm^3$ in volume, the animals were randomised to either the treatment or control group. Mice in the treatment group were administered with compound GB1874 at 50 mg/kg every other day via intraperitoneal injection. Simultaneously animals in the control group were administered with the diluent in the absence of compound. Compound GB1874 was prepared by dissolving it in DMSO to a concentration of 60 mg/mL and diluting it in 5% PEG 300, 5% Tween-80 in saline to a final concentration of 3 mg/mL, 5% DMSO. The length and width of tumours were measured by caliper once every 2 days. Tumour volumes were estimated using the following modified ellipsoidal formula: Tumour volume=½(length×width$^2$). Mice were euthanized when tumours in the control group reaches 2000 $mm^3$.

Results

Generation of β-Cat Structural Models

Figure 1:
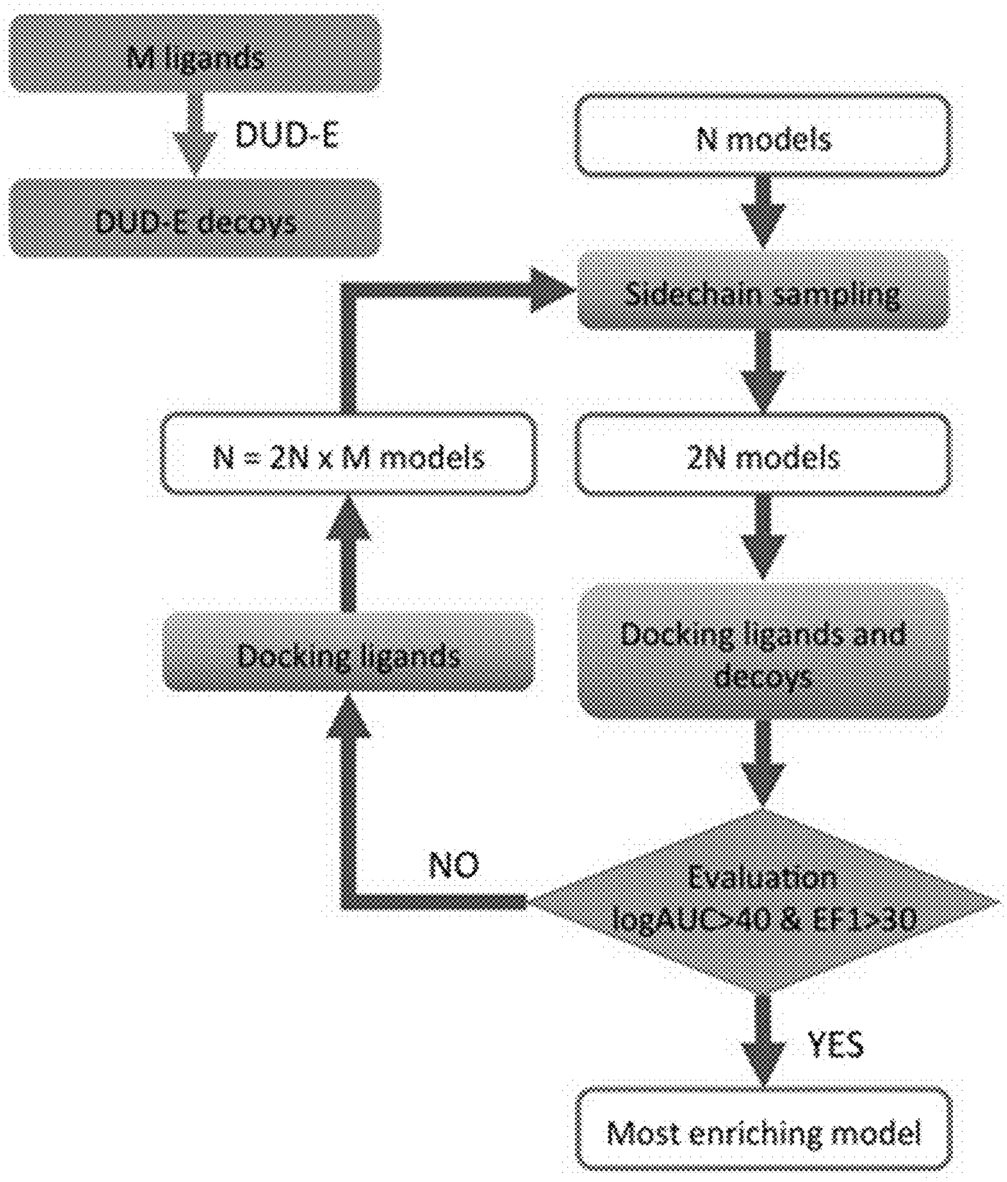
FIG. 1 depicts the modelling and docking platform used in the generation of β-catenin structures for ligand discovery. 3 crystal structures were used as the starting models (N=3). The training library of small molecules contains 3 known inhibitors of β-catenin (M=3). Within one iteration, every target structure would be further optimized in the presence of each of the 3 known ligands docked.

The final structural model of β-cat used in prospective ligand predictions was derived from three β-cat crystal structures including β-cat-Tcf3, β-cat-TCF4, and β-cat-BCL9-TCF4 complexes (PDB code: 1G3J,[18] 1JPW,[19] and 2GL7[20] respectively) through two stages: 1) optimization (training), and 2) blind testing (validation) on the basis of ligand enrichment measured by EF1 and log AUC. The optimization was accomplished by an in-house automated modelling and docking platform (FIG. 1). First, a putative ligand binding site was predicted in the β-cat crystal structure (PDB code: 1JPW) by MetaPocket,[21] overlapping with the charged groove created by β-cat armadillo repeats 4-9, which overlaps the β-cat-TCF4 interaction interface. Therefore, this site was focused on for the current study. Second, the three crystal structures of β-cat were subjected to side-chain sampling by SCWRL,[22] introducing another three structures. This set of 6 β-cat structures served as the starting point of training. Third, to allow a broader exploration of β-cat conformational space, the training library (153 compounds) was docked to all the 6 β-cat structures, evaluated docking performance in terms of the ligand enrichment, and optimized binding site sidechains using PLOP (Protein Local Optimization Program)[23] in the presence of each docked ligand (iCRT3, iCRT5 and iCRT14). This step was iterated till some optimized structures showed ligand enrichment performance better than arbitrary thresholds: log AUC>=40 and EF1>=30.

Prediction of Small Molecule Inhibitors of β-Cat-TCF4 Interaction

Figure 2A:
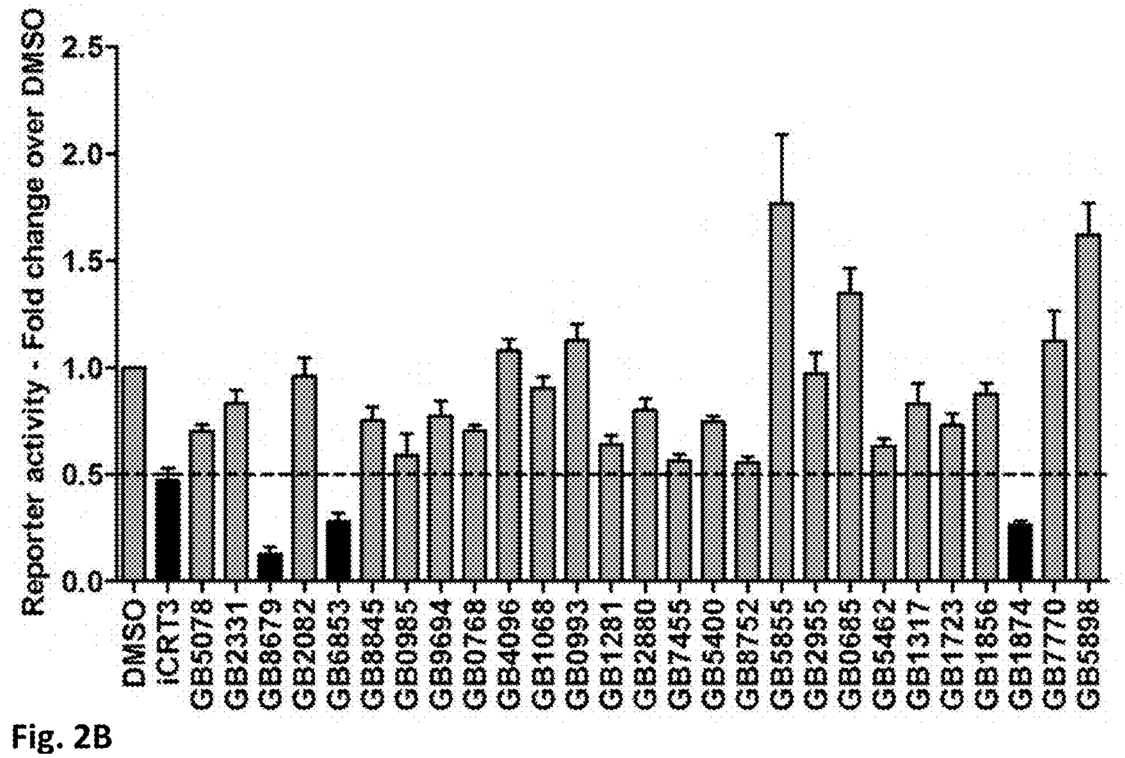
(FIG. 2A) TOPFlash reporter activity of predicted compounds in HEK293T STF cells. The cells were treated with the compounds at 10 IM and simultaneously stimulated with 500 ng/ml of Wnt3A for 24 hr prior to measuring luciferase activity. TOPFlash reporter activities of compound-treated cells were normalized to cell viability and presented as fold change over DMSO treated cells. Error bars represent standard deviation of 4 replicates.
Figure 2B:
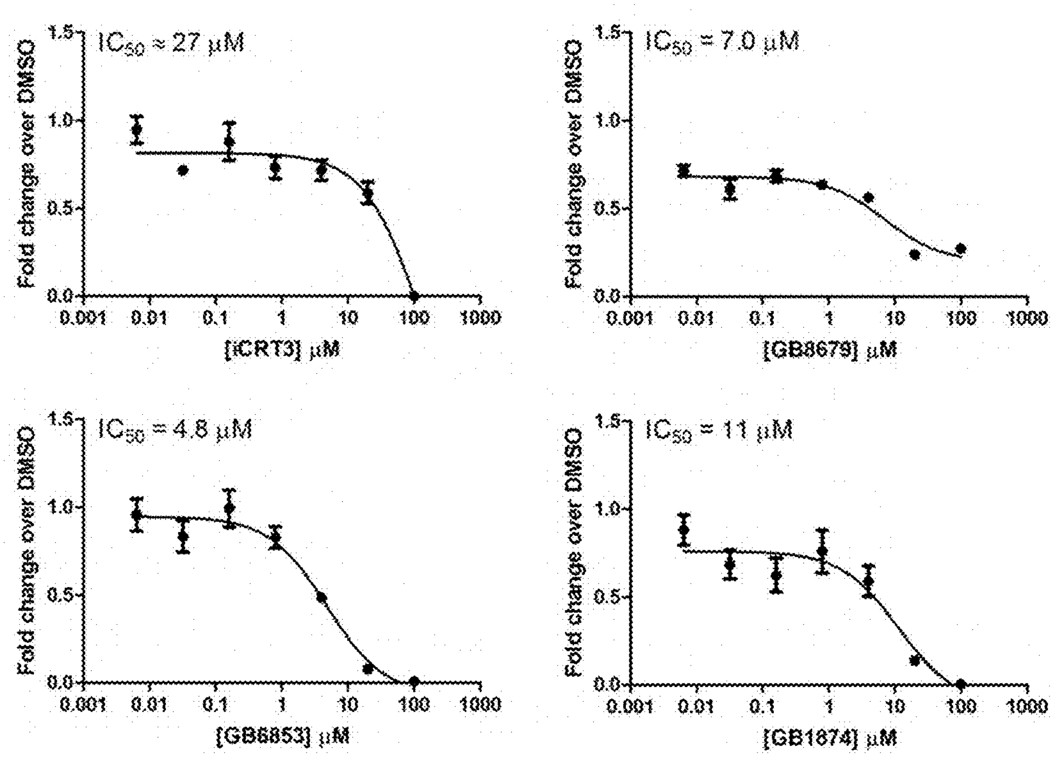
(FIG. 2B) Secondary dose response inhibition of TOPFlash reporter activity by iCRT3 and hit compounds. The STF cells were treated with the different concentrations of compounds and simultaneously stimulated with 500 ng/ml of Wnt3A for 24 hr prior to measuring luciferase activity. Luciferase activities of cells treated with compounds at the various concentrations were first normalized to cell viability at the same concentration and presented as fold change over DMSO treated cells. $IC_{50}$ values were calculated using a four-parameter nonlinear regression. Error bars represent standard deviation of 3 replicates.
Figure 2C:
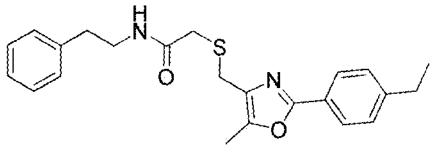
(FIG. 2C) Chemical structures of iCRT3 and the top 3 hit compounds.
Figure 2C:
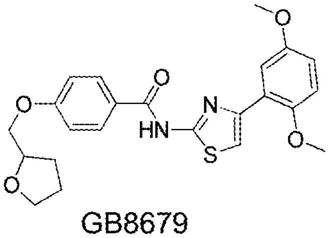
Figure 2C:
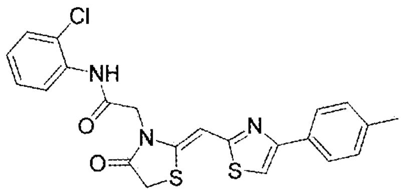
Figure 2C:
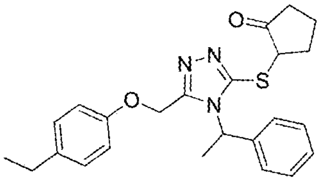
Figure 2D:
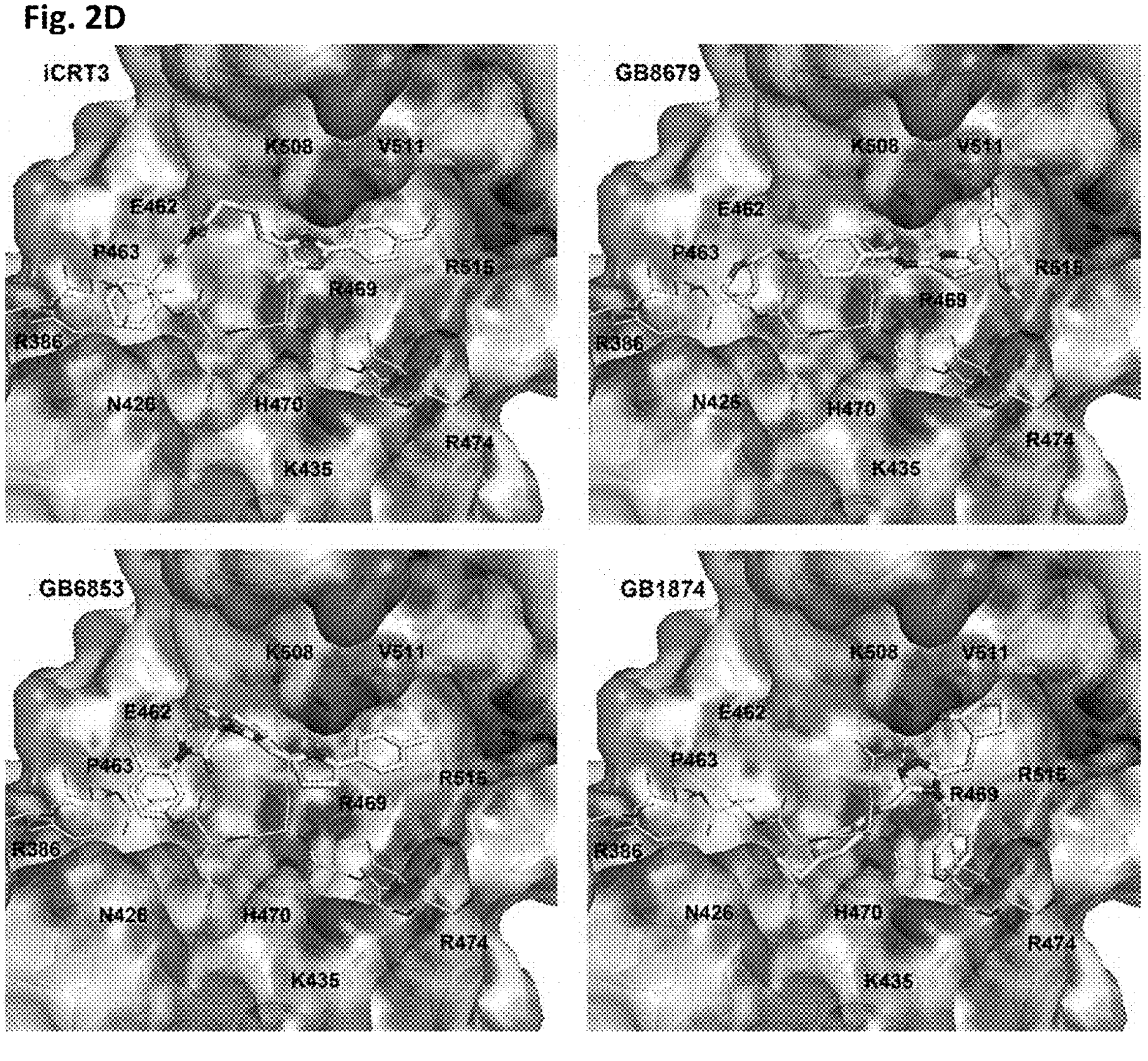
(FIG. 2D) The predicted binding modes of iCRT3 (i), and 3 novel hits found in this study: GB8679 (ii), GB6853 (iii), and GB1874 (iv) in the optimized, most enriching-catenin structure (partial transparent surface). The docked ligands were highlighted (solid stick), and the critical β-catenin binding site residues (partial transparent stick). The TCF4 peptide fragment (solid line) from β-catenin/TCF4 crystal complex structure (PDBID 1JPW) is also shown here to indicate the PPI interface.

The best β-cat structure from the training stage showed an overall ligand enrichment log AUC=44.2, and an early ligand enrichment EF1=33.3 for the training library. The known inhibitor iCRT3 that is the most potent was ranked the best among the 153 compounds in the training library. The interactions of β-cat and iCRT3 in the docking generated complex structure were analyzed. The oxazole group in iCRT3 formed a hydrogen bond with R469 and cation-π interaction with K508 that formed a salt bridge with E17 of TCF4 in the β-cat-TCF4 crystal structure (FIG. 2D). Meanwhile, the phenyl group in iCRT3 packed into the pocket lined by R386, N426, and P463 that have been shown to interact with 119 and F21 of TCF4. In addition, the amide group of iCRT3 that connects the oxazole and the phenyl groups was stabilized by another hydrogen bond with E462 in β-cat, and the ethylphenyl group of iCRT3 filled the pocket lined by K508, V511, and R515.

This most enriched β-cat structure was subjected to a blind testing with the aid of a validation library containing 63 iCRT3 analogues (FIG. 5). 19 ligand candidates were selected from virtual screening considering both docking ranks by DOCK energy scores and docking poses by human intervention (FIG. 5). In the meantime, all the 63 compounds were tested in the Wnt reporter assay, in which HEK 293 cells were stably transfected with TOPFlash reporter (STF cells), at a single concentration and 12 compounds showed activity (data not shown). These 12 compounds were further tested at a range of concentrations against the STF cells, and 5 compounds showed comparable or lower $IC_{50}$ values than the known inhibitor iCRT3 (FIG. 5). In fact, all these 5 strong inhibitors were prioritized by docking as top ligand candidates, suggesting that the most enriched structure generated by training can predict novel ligands.

After functional validation of the methodology for novel ligand prediction, a library of 10240 small molecules (purchased from Enamine) was computationally screened against the most enriched β-cat structure. The 500 (4.0% of the screened library) top-scoring hits were analyzed manually. 27 compounds (FIG. 6) were selected for experimental testing based on three criteria: (1) the disruption of β-cat-TCF4 interactions, (2) the formation of favourable interactions with β-cat residues, e.g. hydrogen bonds, and (3) the chemical novelty of their scaffolds.

Functional Validation of Predicted Inhibitors Using TOP-Flash/Wnt-Reporter Assay The 27 compounds identified from the docking studies were first screened at 10 μM for their ability to inhibit Wnt signalling (FIG. 2A) in the STF-reporter cells. From this screen, 3 compounds were identified, which on average, inhibited Wnt signalling by more than 50% compared to DMSO control while having less than 25% toxicity on the cells (FIG. 7A). Dose response studies of the 3 hit compounds on the STF reporter revealed that they inhibited the Wnt signalling pathway with low micromolar $IC_{50}$ values (FIG. 2B). While they also affected the viability of the reporter cells, the cell viability $EC_{50}$ values were at least 4-fold greater than the reporter $IC_{50}$ values (FIG. 7B). Encouragingly, the 3 hit compounds were about 2- to 5-fold more potent inhibitors of the Wnt pathway compared to our previously reported compound, iCRT3. Interestingly, the three hit compounds have different chemical structures (FIG. 2C).

Specificity of Candidate Inhibitors

To further understand the mechanism of action of the candidate hits, the effect of these small molecule on other signalling pathway activities using reporter cell lines was investigated. The initial screen and dose response studies were carried out in STF reporter lines where Wnt signalling has to be activated via addition of exogenous Wnt3A. The effects on a STF3A reporter cell line, which is a STF reporter line with endogenous expression of Wnt3A, was also examined. Consequently, Wnt signalling is constitutively active in the STF3A reporter cell line. Based on the $IC_{50}$ values obtained, both iCRT3 and compound GB1874 were determined to be potent inhibitors of the Wnt pathway regardless of the initial activation status (Table 1). However while compound GB6853 and GB8679 could potently inhibit the activation of the Wnt pathway (STF $IC_{50}$ values of 4.8 μM and 7.0 μM respectively), they are not effective when Wnt pathway is already activated (STF3A $IC_{50}$ values of >100 μM). This could result from differential abilities of these compounds to disrupt pre-existing (e.g., STF3A cells) versus newly formed (e.g., STF cells) β-cat-TCF4 complexes.

We also investigated the effects of the compounds on a Myc reporter cell line whereby the expression of the luciferase gene is under the control of Myc responsive elements. Since one of the Wnt target genes is Myc, inhibition of Wnt signalling would also result in the inhibition of Myc signalling. The efficacy of the compounds towards the Myc reporter mirrored that of the STF3A reporter whereby potent inhibitors of the Wnt pathway in the STF3A reporter were also potent inhibitors of the Myc reporter (Table 1).

Lastly, the candidate hits were tested against the Hippo pathway reporter whereby TEAD responsive elements drive the expression of luciferase. Since activation of the Hippo pathway results in less TEAD transcriptional activation, compounds which decrease the reporter signal activate the Hippo pathway and vice versa. Interestingly, it was found that the Hippo pathway can be activated by iCRT3 and that compound GB8679 is a potent inhibitor of the Hippo pathway (Table 1). Since the Wnt pathway can crosstalk with the Hippo pathway,[24] it was suspected that the inhibition of Hippo signalling by GB8679 could indirectly affect its effectiveness in reducing the expression of Wnt target genes.

In Silico Predicted Distinct Binding Modes of 3 Candidate Small Molecule Binders of β-Cat The predicted binding modes of two hits GB8679 and GB6853 in β-cat are similar to that of iCRT3. For example, both compounds occupied the two pockets lined by R386, N426, P463, and by K508, V511, R515 respectively, with their bulky hydrophobic groups. Meanwhile, the cleft between K508 and R469 was also filled by the thiazole group in both compounds, with hydrogen bond and salt bridge formation (FIG. 2D). The third hit GB1874, however, presented a different binding mode from iCRT3 and the other two hits. It still packed into the cleft between K508 and R469 with its triazole group, and the two pockets lined by R386, N426, P463, and K508, V511, R515 with its hydrophobic groups. In addition, an ethylphenyl group of GB1874 packed into the pocket lined by H470, R474, and K435. Strikingly, this pocket in β-cat-TCF4 crystal complex structure is occupied by TCF4 D16 residue that forms a salt bridge with K435 in β-cat, and represents a key β-cat-TCF4 interaction.[25] Single amino acid substitution of D16 on TCF4 or K435 on β-cat is sufficient to disrupt their interaction and markedly reduce downstream transcriptional activity.[25-26] Taken together, it was hypothesized that this unique binding mode of GB1874 would allow it to more potently disrupt β-cat-TCF4 interactions, as compared to iCRT3 and the other two hits.

Figure 3A:
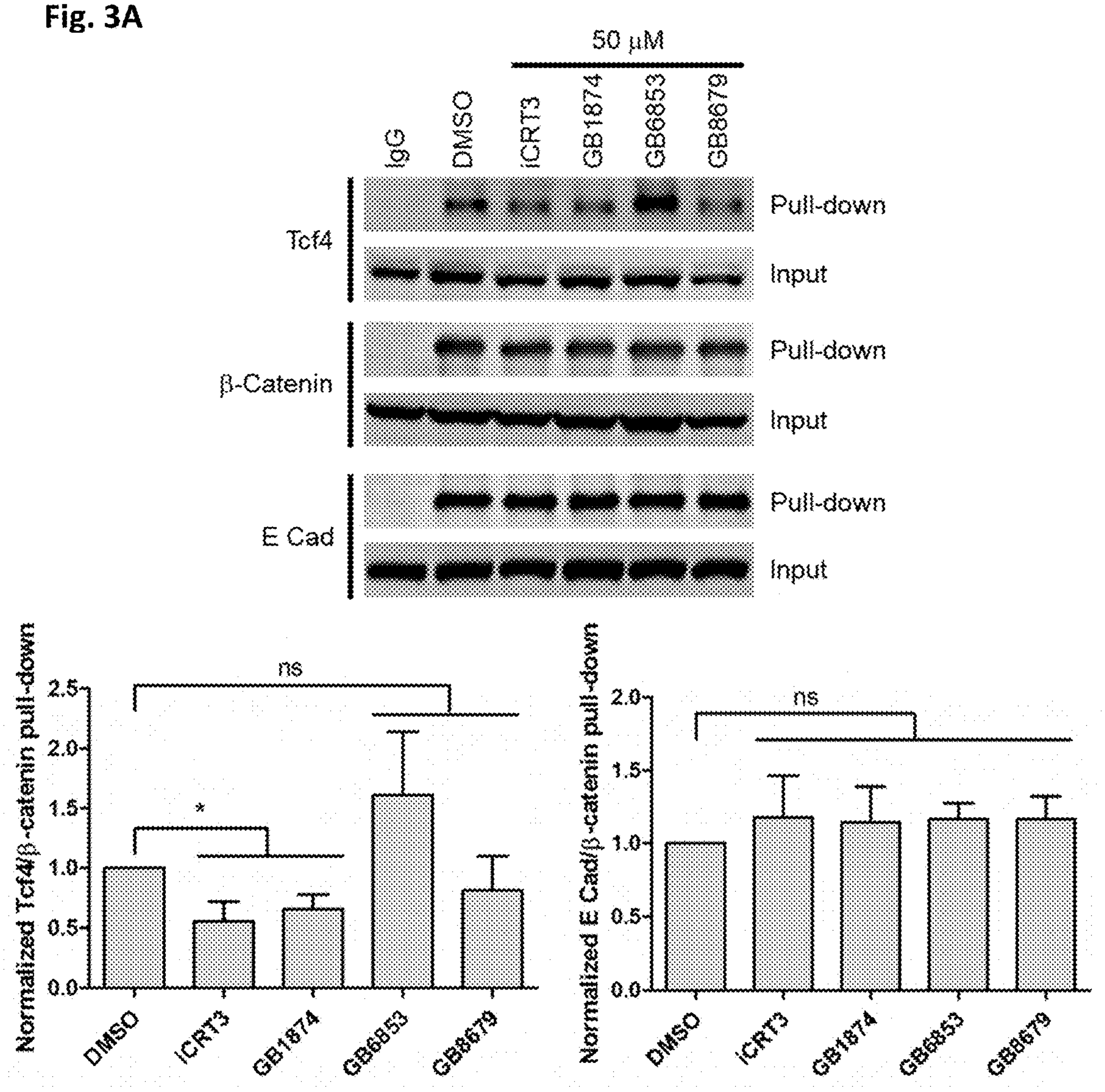
(FIG. 3A) Co-immunoprecipitation of β-catenin and its endogenous binding partners. HCT116 cells were treated for 18 hr with the hit compounds at the indicated concentrations. β-catenin was immunoprecipitated from protein lysates of the treated cells and the amount of TCF4 and E cadherin bound to β-catenin was analyzed via Western blot (top panel). Quantification of TCF4 (bottom right panel) or E cadherin (bottom left panel) bound to β-catenin under different treatment and normalized against DMSO treated cells. Error bars represent standard deviation of n=4 independent experiments. Two-tailed paired Student's t-test was carried out between DMSO control and compound treatment. *$P<0.05$, ns $P>0.05$.

Hit Compounds Disrupt β-Cat-TCF4 Interaction and Reduce Expression of Wnt Target Genes As the compounds were identified through in silico docking studies on the β-cat protein, the other compounds ability to disrupt the β-cat-TCF4 interaction in biologically relevant cell lines was investigated. Consequently, co-immunoprecipitation (co-IP) of β-cat and its interacting partners in HCT116 CRC cells was carried out. Western blot analysis of the proteins bound to β-cat under compound treatment revealed that amongst the 3 hit compounds, only compound GB1874 could reduce the β-cat-TCF4 interaction to the same extent as iCRT3 (FIG. 3A). Encouragingly it was observed that while compound GB1874 affected the β-cat-TCF4 interaction, it has minimal effect on the β-cat-ECAD interaction (FIG. 3A).

Figure 3B:
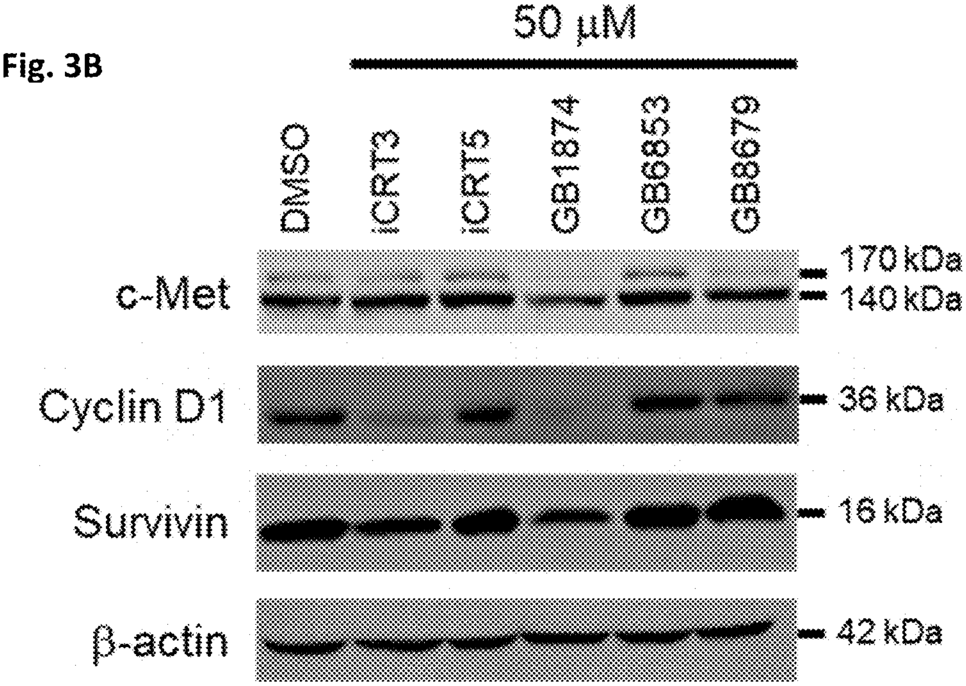
(FIG. 3B) HCT116 cells were treated for 18 hr with either DMSO or compounds at 50 μM. Expression of Wnt target proteins c-Met, cyclin D1, and survivin were determined by Western blotting.
Figure 3C:
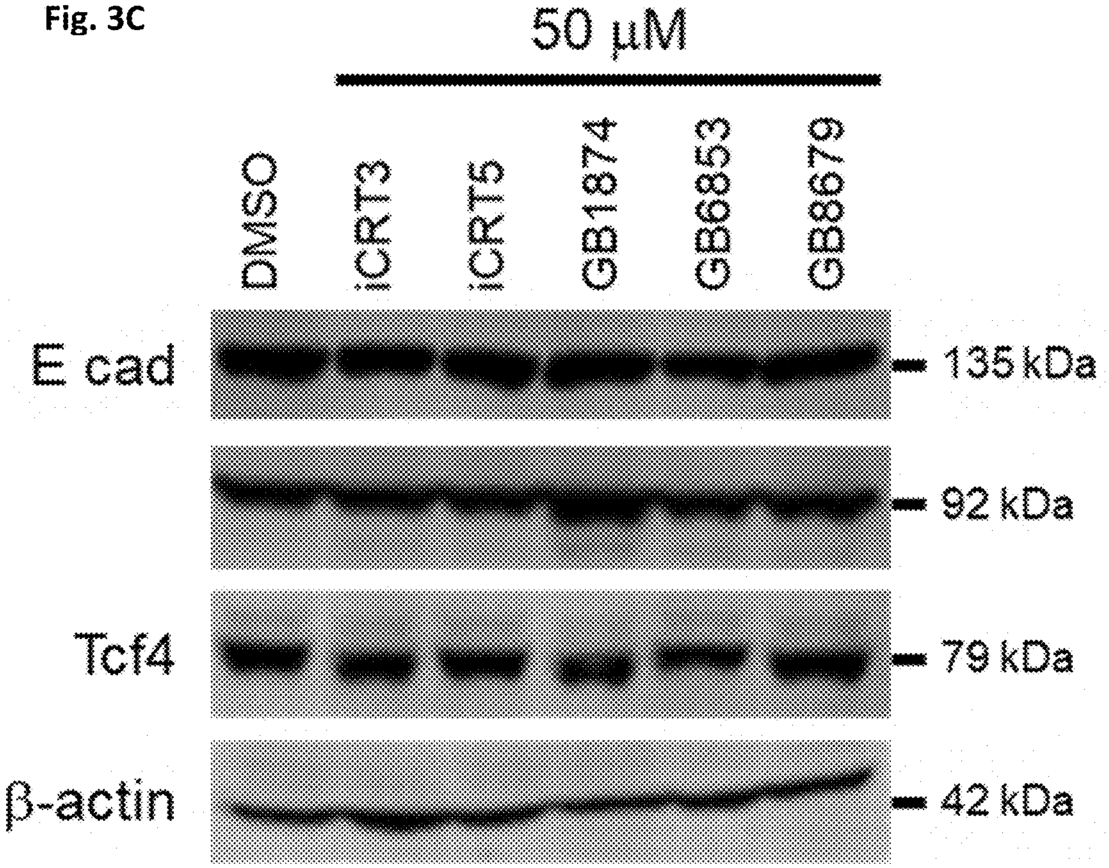
(FIG. 3C) HCT116 cells were treated for 18 hr with either DMSO or compounds at 50 μM. Expression of Wnt pathway related proteins E cadherin, β-catenin, and TCF4 were determined by Western blotting.

Subsequently, the effects of the hit compounds on the expression of Wnt target genes was investigated. HCT 116 cells were treated with the compounds at 50 μM and the expression of Wnt target genes, including c-Met, cyclin D1 and survivin were analysed by Western blotting. Compound GB1874 was the most effective at reducing the expression of these proteins (FIG. 3B). In fact, the reduction of Wnt target protein expression by compound GB1874 was comparable to that of iCRT3. Additionally while compound GB1874 reduced the expression of Wnt target genes, it had minimal effect on the expression of β-cat itself, or the expression of its partner proteins, such as ECAD and TCF4 (FIG. 3C). These results suggest that GB1874 can modulate the nuclear transcriptional function of β-cat by specifically disrupting β-cat-TCF4 interaction, without influencing its membrane function at the E-cad-mediated adherens junction.

On the other hand, compounds GB6853 and GB8679 had minimal effect on the expression of the Wnt target genes investigated (FIG. 3B). These compounds were also not as effective as compound GB1874 in disrupting the β-cat-TCF4 interaction (FIG. 3A). These results, together with their lack of inhibitory activity in the STF3A report cell line (Table 1), suggest that they are unable to inhibit the Wnt pathway in cells where Wnt signalling is already active.

Compound GB1874 Disrupts the β-Cat-TCF4 Interaction In Vitro

Figure 3D:
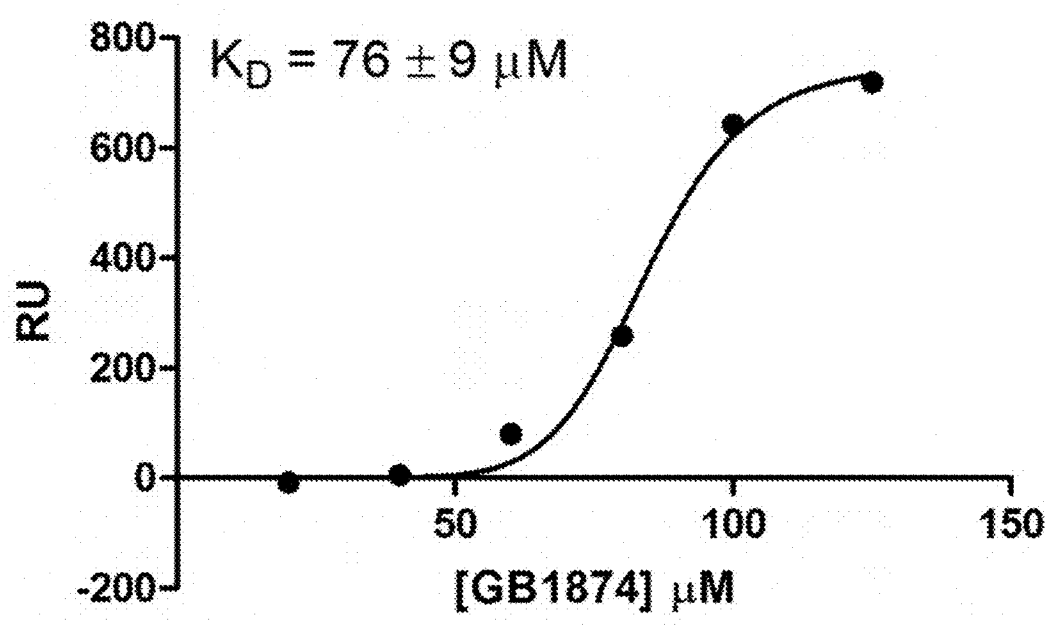
(FIG. 3D) Representative binding curve of compound GB1874 on β-catenin from surface plasmon resonance (SPR) studies. Steady-state response values were plotted against the respective concentrations of compound GB1874 and the dissociation constant KD (n=3) was calculated using a specific binding with Hill slope curve fitting equation.

Since GB1874 compound was predicted to bind β-cat via in silico docking studies, experiments were conducted to determine if it could interact with purified β-cat in vitro and inhibit its interaction with TCF4. Surface plasmon resonance (SPR) studies were employed with purified proteins encoding for β-cat (ARM-domain repeat region) and the TCF4 N-terminal domain, which is known to interact with β-cat. The purified β-cat protein was first immobilized onto a SPR sensor chip and injected different concentrations of compound GB1874 over β-cat. From the sensorgrams (FIG. 8A), a dose dependent binding of compound GB1874 to β-cat was observed. A plot of steady state response values against concentration of compound GB1874 indicated that the compound binds to β-cat with a $K_D$ of 76±13 μM (n=3, FIG. 3D). However the Hill slope of the best fit curve is greater than 1, suggesting that compound GB1874 binds to multiple sites on β-cat with positive cooperativity.

Figure 3E:
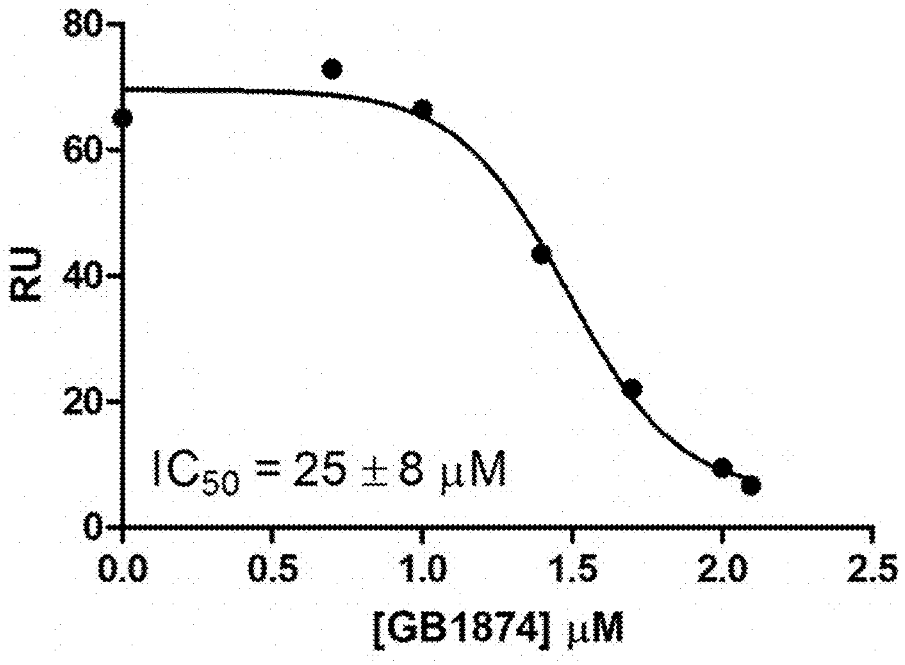
(FIG. 3E) SPR dose response inhibition of β-catenin and GST-TCF4 binding by compound GB1874. The $IC_{50}$ value (n=2) was calculated using a four-parameter nonlinear regression.

To ascertain if compound GB1874 can directly inhibit the interaction between β-cat and TCF4 in vitro, a SPR competition experiment was developed. Instead of β-cat, TCF4 N-terminal domain was immobilized onto a SPR sensor chip. 50 nM β-cat, pre-incubated with different concentrations of compound GB1874, was then injected over the TCF4 N-terminal domain. As is evident from the sensograms (FIG. 8B), compound GB1874 was found to inhibit the interaction between β-cat and TCF4 with an $IC_{50}$ value of 25±8 μM (n=2) (FIG. 3E).

Candidate Hit Compounds Affect Proliferation and Stemness of 'Wnt-Addicted' Cancer Cells Apart from disrupting the β-cat-TCF4 interaction and reducing the expression of Wnt target genes, experiments were conducted to determine whether the hit compounds elicit phenotypes that are reminiscent of reduced Wnt activity in biologically relevant cancer cell lines. First, the effect of candidate compounds GB6853, GB8679, and GB1874 on HCT116 colorectal cancer (CRC) cells was investigated. HCT116 cells possess a heterozygous mutation in the β-cat gene which results in the deletion of the Ser45 residue in the protein. Ser45 is the site for the priming phosphorylation by CK1a, a key member of the destruction complex, which subsequently targets β-cat for proteasomal degradation. Mutation in Ser45 therefore results in constitutively active Wnt signalling as the mutant β-cat cannot be degraded. It was hypothesized that inhibition of Wnt signalling downstream of β-cat in HCT116 cells would have greater efficacy on their growth.

Figure 4A:
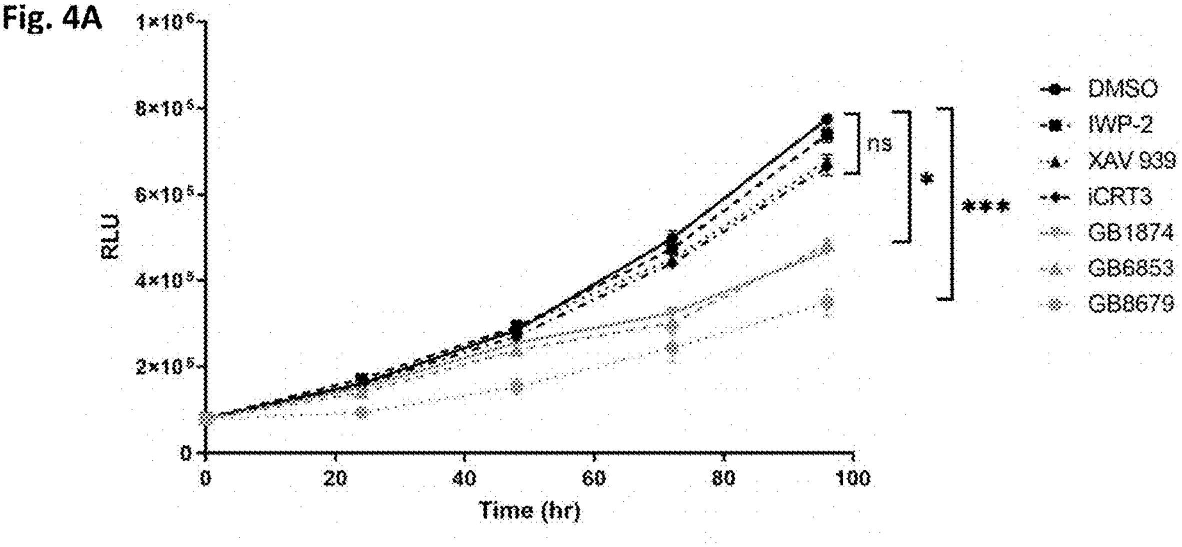
(FIG. 4A) Growth curves of HCT116 cells treated daily with compounds at 10 μM. One-way repeated measures ANOVA with Dunnett's multiple comparison test was carried out to determine the significance between compound treatment and DMSO control. *$P<0.05$, *$P<0.001$.
Figure 4B:
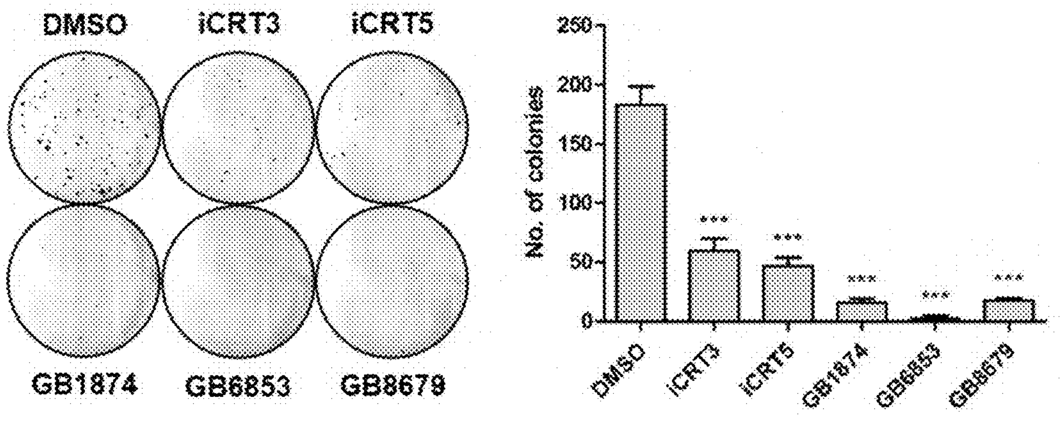
(FIG. 4B) Effects of hit compounds on colony formation of HCT116 cells. HCT116 cells were grown in 6-well plates and treated with either DMSO or the compounds at 30 μM for 7 days, following which the cells were fixed and stained with crystal violet. The number of colonies obtained were counted. Two-tailed Student's t-test was carried out between compound treatment and DMSO control. *$P<0.001$.
Figure 4C:
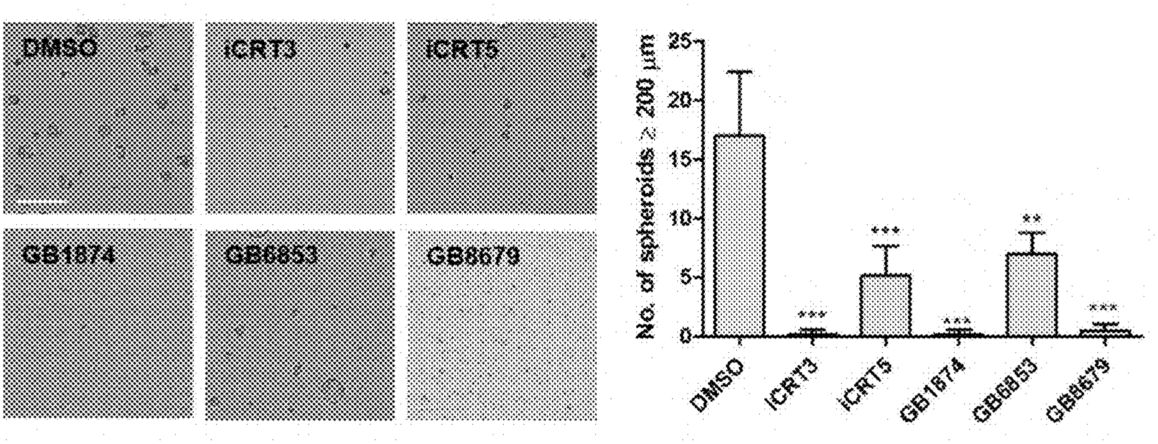
(FIG. 4C) Effects of hit compounds on spheroid formation of HCT116 cells. HCT116 cells were grown in ultra-low attachment 96-well plates and treated with either DMSO or the compounds at 30 UM for 14 days, following which the number of spheroids ≥200 μm in size was determined. Two-tailed Student's t-test was carried out between compound treatment and DMSO control. *$P<0.001$, $P<0.01$. Scale bar represents 1 mm.

HCT116 cells were treated daily with 10 μM of each compound and the growth was monitored using CellTiter-Glo viability assay. For comparison, compounds such as IWP-2, XAV 939, and iCRT3 which target different components along the Wnt signal transduction cascade were included.[27] As shown in FIG. 4A, treatment with either of the three hit compounds (GB1874, GB6853, and GB8679) effectively inhibited the growth of HCT116 cells. Notably they were all more effective than iCRT3 in growth inhibition assays. Compounds IWP-2 and XAV939 (inhibitors of Porcupine and Tankyrase respectively), which inhibit Wnt signalling upstream of the β-cat-TCF4 interaction, were less effective at inhibiting the growth of HCT116 cells. Compounds GB8679, GB6853, and GB1874 at 30 μM could also markedly reduce survival of the cancer stem-like cells within the HCT116 population as evidenced by their effect on colony forming efficiency (FIG. 4B), and spheroid formation assay (FIG. 4C). Additionally, the hit compounds also affected, albeit to different extents, the spheroid formation of APC mutant CRC cell lines, DLD-1 and SW480 (FIGS. 9A and 9B). Subsequently the effects of the compounds on the viability of the CRC cells was investigated. From the $EC_{50}$ values against HCT116, DLD-1, and SW480 cell lines (Table 2), compound GB1874 was most potent against the CRC cell lines followed by compound GB8679.

GB1874 Inhibits Growth of Mouse Tumor Xenografts

Figure 4D:
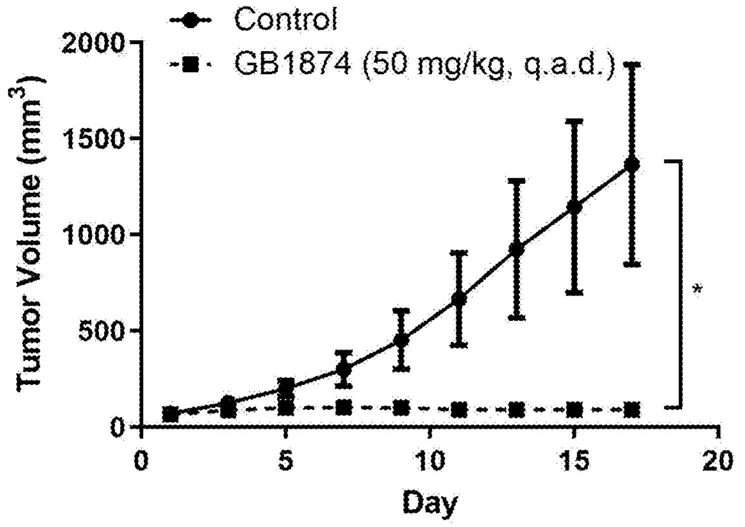
(FIG. 4D) NSG mice xenografted with HCT116 cells were treated with vehicle control (n=6) or 50 mg/kg GB1874 (n=6) via i.p. every other day for 2 weeks. Tumor volumes were monitored over time. Two-tailed Student's t-test was carried out between control and treatment at day 17. *P<0.05.

Based on the above studies, compound GB1874 was identified to be the most potent compound against Wnt driven CRC cells. To investigate its efficacy in vivo, HCT116 cells were inoculated into the flanks of NSG mice. Subsequently tumor-bearing mice were treated with either vehicle control or compound GB1874 at 50 mg/kg every other day (q.a.d.) via i.p injection. compound GB1874 effectively inhibited the growth of HCT116 xenografts in vivo (FIG. 4D) while causing minimal systemic toxicity in the mice (FIG. 9C).

TABLE 1

| Effects of hit compounds on various signalling pathways. | | | | |
|---|---|---|---|---|
| | $IC_{50}$ (μM) | | | |
| Compound | Wnt (STF) | Wnt (STF3A) | Myc | Hippo |
| iCRT3 | 27 | 64 | 50 | 1.6 (activation) |
| GB1874 | 11 | 26 | 32 | >100 |
| GB6853 | 4.8 | >100 | >100 | >100 |
| GB8679 | 7.0 | >100 | >100 | 10 |

TABLE 2

| Effects of hit compounds on the viability of Wnt driven CRC cells. | | | |
|---|---|---|---|
| | $EC_{50}$ (μM) | | |
| Compound | HCT116 | DLD-1 | SW480 |
| iCRT3 | 39 | 48 | 64 |
| GB1874 | 45 | 28 | 24 |
| GB6853 | >100 | >100 | >100 |
| GB8679 | 100 | 53 | >100 |

Using the structure of GB1874 as a scaffold, chemical databases were searched for analogues of GB1874. These compounds were then docked onto our in silico model of beta-catenin to predict strong candidate binders of beta-catenin. From this, 8 structural analogues of GB1874 were identified, which were tested.

We first tested these compounds for the ability to inhibit Wnt reporter activity using the STF and STF3A reporter cells (Table 3). In general, the inhibition $IC_{50}$ values against the STF cells were lower compared to the corresponding values against the STF3A cells, indicating that these compounds were less active against biological systems with constitutive Wnt activation. The exception was GB1874A in which it was more potent against the STF3A cells compared to the STF cells.

Comparing the $IC_{50}$ value of GB1874 (STF $IC_{50}$=6.8 M, STF3A $IC_{50}$=27 μM) with that of GB1874F (STF $IC_{50}$=5.4 M, STF3A $IC_{50}$=10 μM), GB1874G (STF $IC_{50}$=3.9 M, STF3A $IC_{50}$=6.7 μM), and GB1874H (STF $IC_{50}$=5.0 μM, STF3A $IC_{50}$=11 μM), it was observed that increasing the size of the C3 substituent of 1,2,4-triazole did not affect the compounds' activity against the STF or STF3A reporters. As the new analogues of GB1874 were mostly different at the C3 substituent of the 1,2,4-triazole, the effects of changing substituents at the other positions could not be deduced. Consequently, to obtain a better understanding of the structure activity relationship of GB1874, more analogues of GB1874 would need to be purchased or synthesized.

TABLE 3

| Structural analogues of GB1874 and their activities against the STF and STF3A reporter cell lines. | | | | | |
|---|---|---|---|---|---|
| | | STF | | STF3A | |
| Compound | Structure | Inhibition $IC_{50}$ (μM) | Toxicity $IC_{50}$ (μM) | Inhibition $IC_{50}$ (μM) | Toxicity $IC_{50}$ (μM) |
| iCRT3 | 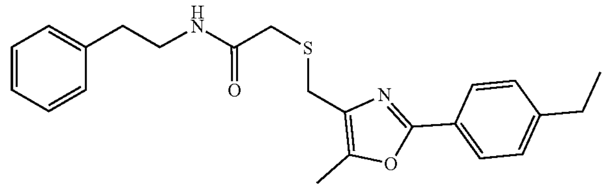 [SMILES: CCc1ccc(-c2nc(CSCC(=O)NCCc3ccccc3)c(C)o2)cc1] | 11 | 88 | 42 | 74 |
| GB1874 | 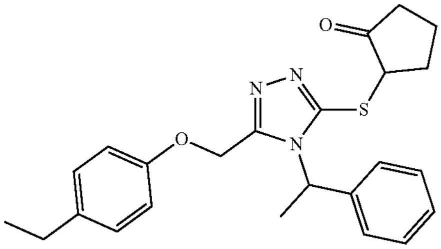 [SMILES: CCc1ccc(OCc2nnc(SC3CCCC3=O)n2C(C)c2ccccc2)cc1] | 6.8 | 66 | 27 | 64 |
| GB1874A | 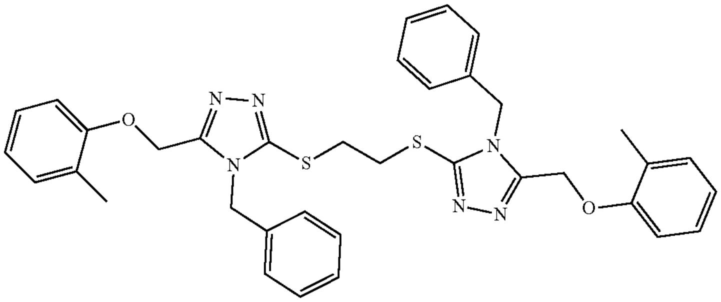 [SMILES: Cc1ccccc1OCc1nnc(SCCSc2nnc(COc3ccccc3C)n2Cc2ccccc2)n1Cc1ccccc1] | 28 | >100 | 1.2 | >100 |

TABLE 3-continued
Structural analogues of GB1874 and their activities against the STF and STF3A reporter cell lines.
| Compound | Structure | STF Inhibition $IC_{50}$ (μM) | STF Toxicity $IC_{50}$ (μM) | STF3A Inhibition $IC_{50}$ (μM) | STF3A Toxicity $IC_{50}$ (μM) |
|---|---|---|---|---|---|
| GB1874B | 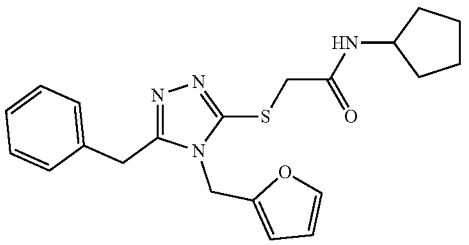 [SMILES: O=C(CSc1nnc(Cc2ccccc2)n1Cc1ccco1)NC1CCCC1] | 48 | >100 | >100 | >100 |
| GB1874C | 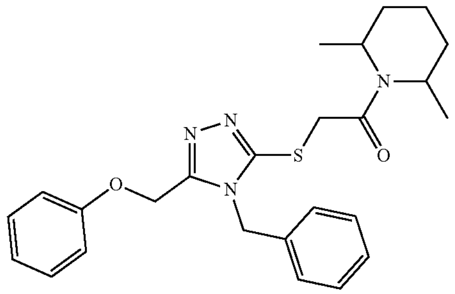 [SMILES: CC1CCCC(C)N1C(=O)CSc1nnc(COc2ccccc2)n1Cc1ccccc1] | 7.6 | 76 | 46 | 78 |
| GB1874D | 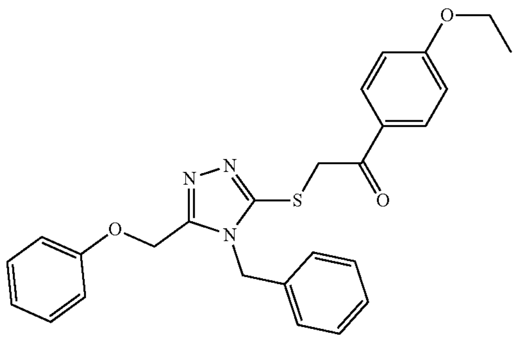 [SMILES: CCOc1ccc(C(=O)CSc2nnc(COc3ccccc3)n2Cc2ccccc2)cc1] | 21 | >100 | 21 | 25 |
| GB1874E | 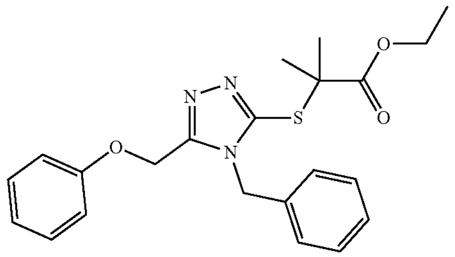 [SMILES: CCOC(=O)C(C)(C)Sc1nnc(COc2ccccc2)n1Cc1ccccc1] | 12 | 71 | 16 | 100 |

TABLE 3-continued

Structural analogues of GB1874 and their activities against the STF and STF3A reporter cell lines.

| Compound | Structure | STF Inhibition $IC_{50}$ (μM) | STF Toxicity $IC_{50}$ (μM) | STF3A Inhibition $IC_{50}$ (μM) | STF3A Toxicity $IC_{50}$ (μM) |
|---|---|---|---|---|---|
| GB1874F | 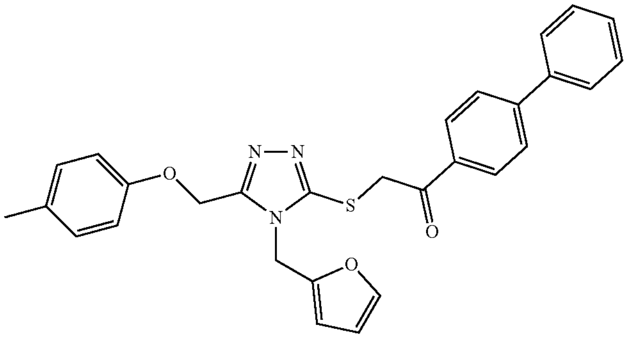 [SMILES: Cc1ccc(OCc2nnc(SCC(=O)c3ccc(-c4ccccc4)cc3)n2Cc2ccco2)cc1] | 5.4 | 100 | 10 | >100 |
| GB1874G | 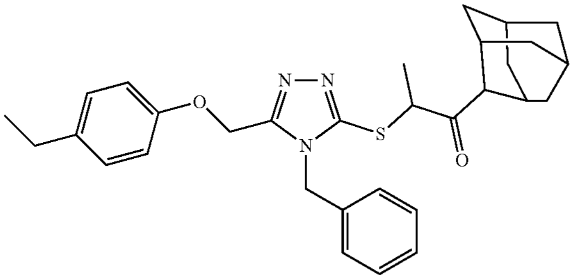 [SMILES: CCc1ccc(OCc2nnc(SC(C)C(=O)C3C4CC5CC(C4)CC3C5)n2Cc2ccccc2)cc1] | 3.9 | >100 | 6.7 | >100 |
| GB1874H | 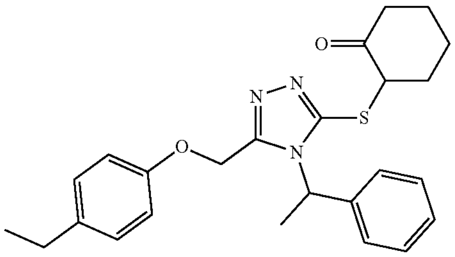 [SMILES: CCc1ccc(OCc2nnc(SC3CCCCC3=O)n2C(C)c2ccccc2)cc1] | 5.0 | 49 | 11 | 46 |

The effects of the GB1874 analogues were tested on the expression of Wnt target genes in HCT116 CRC cells. From the results obtained (FIG. 5), it was observed that the extent of Wnt target gene downregulation correlates with the compounds' potency in inhibiting the STF reporter. The most potent compounds were iCRT3, GB1874, GB1874C, GB1874E, GB1874F, GB1874G, and GB1874H. These compounds potently inhibit Wnt target genes such as AXIN2, BIRC5, BMP4, and CCND1 while having a lesser effect on beta-catenin (CTNNB1) gene expression.

We also tested our top hit compound, GB1874, on primary patient-derived colorectal cancer (CRC) cell lines (Table 4). GB1874 was found to be more potent against the primary CRC cell lines compared to Tankyrase inhibitor XAV939.

TABLE 4

$EC_{50}$ values of GB1874 and XAV939 against primary patient-derived colorectal cancer cell lines.

| Cell line | Site | $EC_{50}$ (μM) GB1874 | $EC_{50}$ (μM) XAV939 |
|---|---|---|---|
| CRC948 | Primary | 17 | >250 |
| CRC1177 | Primary | 19 | 250 |
| CRC1258 | Liver Met | 27 | 70 |
| CRC1414 | Primary | 42 | >250 |
| CRC1463 | Primary | 27 | 250 |
| CRC1489 | Primary | 41 | 105 |
| CRC1671 | Primary | 30 | >250 |
| CRC1707 | Primary | 19 | 135 |

TABLE 4-continued

EC$_{50}$ values of GB1874 and XAV939 against primary patient-derived colorectal cancer cell lines.

| Cell line | Site | EC$_{50}$ (μM) GB1874 | XAV939 |
|---|---|---|---|
| CRC1775 | Primary | 74 | >250 |
| CRC1837 | Liver Met | 21 | >250 |
| CRC1846 | Primary | 17 | 239 |
| CRC1850 | Liver Met | 37 | 208 |
| CRC2001 | Primary | 25 | >250 |
| CRC2255 | Primary | 20 | >250 |
| CRC2367 | Primary | 20 | >250 |
| CRC2413 | Primary | 16 | 200 |
| CRC2423 | Primary | 30 | 250 |
| CRC2440 | Primary | 16 | 75 |

The HCT116 xenograft tumours obtained from the in vivo studies were analysed. As shown in FIG. 4D and shown again in FIG. 11A, treatment of HCT116 xenografts with GB1874 at 50 mg/kg every other day (q.a.d.) via i.p, inhibited the growth of HCT116 xenografts. Through immunohistochemical staining and quantification, it was shown that the inhibition of tumour growth was related to reduction in the expression of Wnt target gene, cyclin D1, as well as the proliferation marker, Ki67 (FIG. 11B).

INDUSTRIAL APPLICABILITY

The compounds disclosed herein can be used to inhibit β-cat or disrupt the interaction of β-cat and TCF4 and therefore can be used in the treatment of a disease or health condition is selected from the group consisting of cancer, neurodegenerative, a metabolic disease, a cardiovascular disease, fibrosis, and a bone disease.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

REFERENCES

1. Polakis, 2000, Genes Dev. 14:1837-1851.
2. Morin et al., 1997, Science 275:1787-1790.
3. Rubinfeld et al., 1997, Science 275:1790-1792.
4. Koch et al., 1999, Cancer Res. 59:269-273.
5. Zurawel et al, 1998, Cancer Res. 58:896-899.
6. Voeller et al, 1998, Cancer Res. 58:2520-2523.
7. Schlosshauer et al., 2000, Mod. Pathol. 13:1066-1071.
8. Mirabelli-Primdahl et al, 1999, Cancer Res. 59:3346-3351.
9. Saegusa and Okayasu, 2001, J. Pathol. 194:59-67.
10. Wu et al., 2001, Cancer Res. 61:8247-8255.
11. Hayes et al., 2008, Clin. Cancer Res. 14:4038-4044.
12. Gonsalves F C, Klein K, Carson B B, Katz S, Ekas L A, Evans S, et al. An RNAi-based chemical genetic screen identifies three small-molecule inhibitors of the Wnt/wingless signalling pathway. *Proc Nat. Acad Sci USA* 2011; 108, 5954-63.
13. Irwin J J, Sterling T, Mysinger M M, Bolstad E S, Coleman R G. ZINC: a free tool to discover chemistry for biology. *J Chem Inf Model* 2012; 52: 1757-68.
14. Mysinger M M, Carchia M, Irwin J J, Shoichet B K. Directory of useful decoys, enhanced (DUD-E): better ligands and decoys for better benchmarking. *J Med Chem* 2012; 55: 6582-94.
15. Kuntz I D, Blaney J M, Oatley S J, Langridge R, Ferrin T E. A geometric approach to macromolecule-ligand interactions. *J Mol Biol* 1982; 161: 269-88.
16. Mysinger M M, Shoichet B K. Rapid context-dependent ligand desolvation in molecular docking. *J Chem Inf Model* 2010; 50: 1561-73.
17. Fan H, Irwin J J, Webb B M, Klebe G, Shoichet B K, Sali A. Molecular docking screens using comparative models of proteins. *J Chem Inf Model* 2009; 49: 2512-27.
18. Graham T A, Weaver C, Mao F, Kimelman D, Xu W. Crystal structure of a beta-catenin/TCF4 complex. *Cell* 2000; 103: 885-96.
19. Poy F, Lepourcelet M, Shivdasani R A, Eck M J. Structure of a human TCF4-β-catenin complex. *Nat Struct Biol* 2001; 8: 1053-7.
20. Sampietro J, Dahlberg C L, Cho U S, Hinds T R, Kimelman D, Xu W. Crystal structure of a beta-catenin/BCL9/TCF4 complex. *Mol Cell* 2006; 24: 293-300.
21. Zhang Z, Li Y, Lin B, Schroeder M, Huang B. Identification of cavities on protein surface using multiple computational approaches for drug binding site prediction. *Bioinformatics* 2011; 27: 2083-8.
22. Krivov G G, Shapovalov M V, Dunbrack R L Jr. Improved prediction of protein side-chain conformations with SCWRL4. *Proteins* 2009; 77: 778-95.
23. Sherman W, Day T, Jacobson M P, Friesner R A, Farid R. Novel procedure for modeling ligand/receptor induced fit effects. *J Med Chem* 2006; 49: 534-53.
24. Piccolo S, Dupont S, Cordenonsi M. The biology of Yap/TAZ: Hippo signalling and beyond. *Physiol Rev* 2014; 94: 1287-312.
25. Fasolini M, Wu X, Flocco M, Trosset J Y, Oppermann U, Knapp S. Hot Spots in TCF4 for the Interaction with β-Catenin. *J Biol Chem* 2003; 278: 21092-8.
26. Liu J, Wang H, Zuo Y, Farmer S R. Functional Interaction between Peroxisome Proliferator-Activated Receptor γ and β-Catenin. *Mol Cell Biol* 2006; 26: 5827-37.
27. Kahn M. Can we safely target the WNT pathway? *Nat Rev Drug Discovery* 2014; 13: 513-32.

What is claimed:

1. A method of inhibiting β-cat or disrupting the interaction between β-cat and TCF4, the method comprising:

contacting β-cat with a compound selected from the group consisting of:

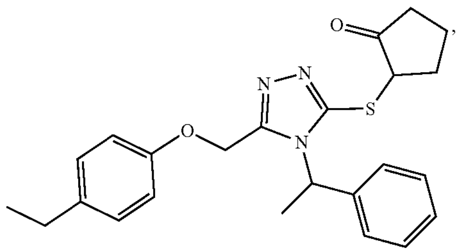

,

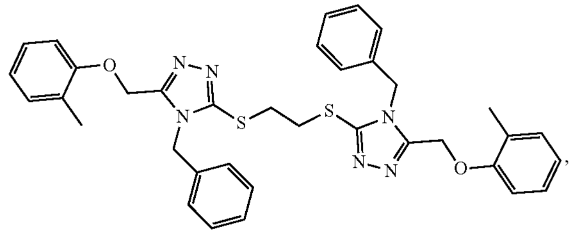

,

-continued
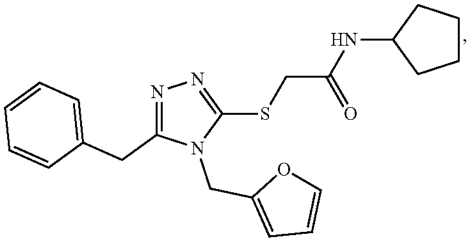
,
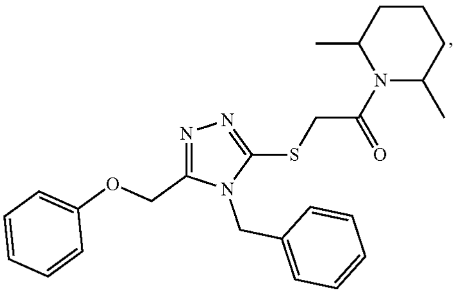
,
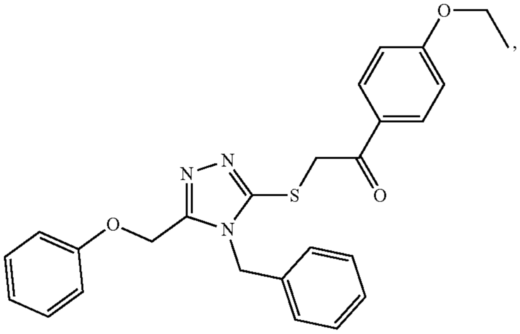
,
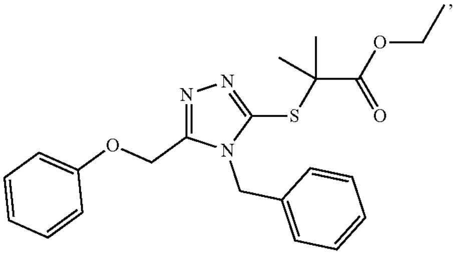
,
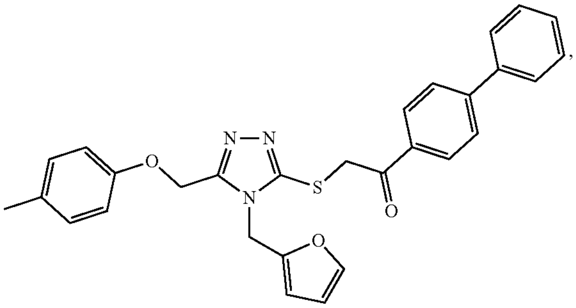
,
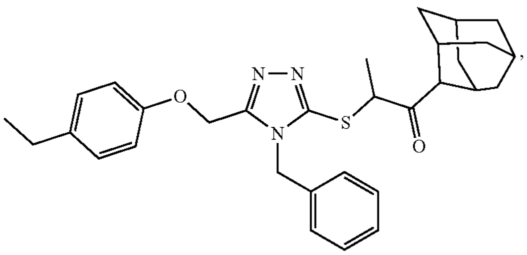
, and
-continued
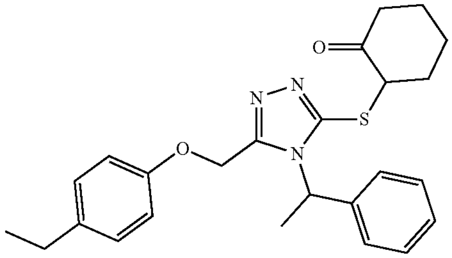
or
a pharmaceutically acceptable salt thereof.
2. A method of treating cancer in a subject in need thereof, the method comprising administering a therapeutically effective amount of a compound selected from the group consisting of:
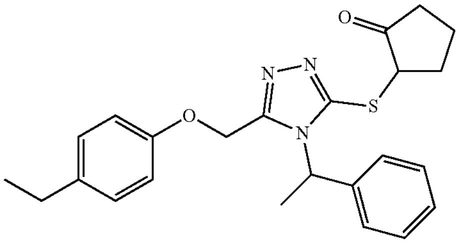
,
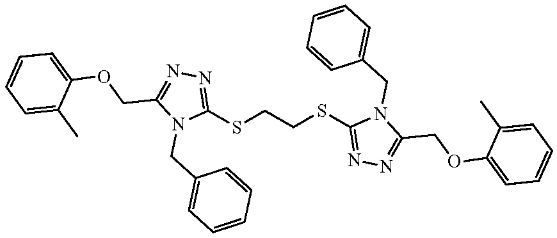
,
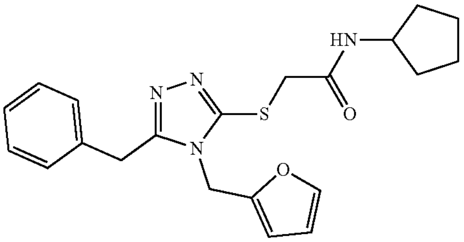
,
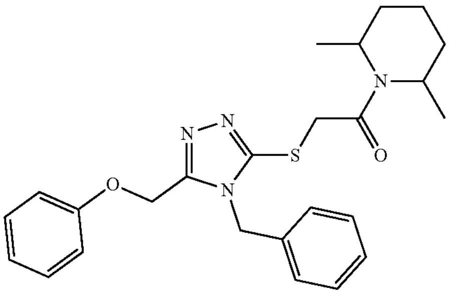
, -continued
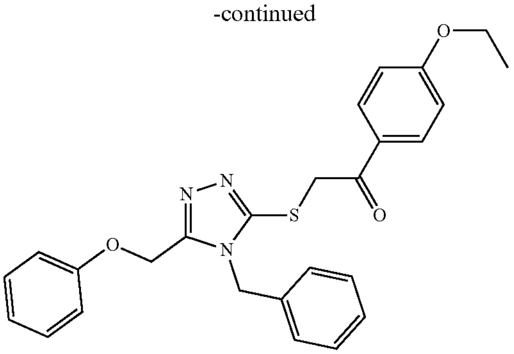
,
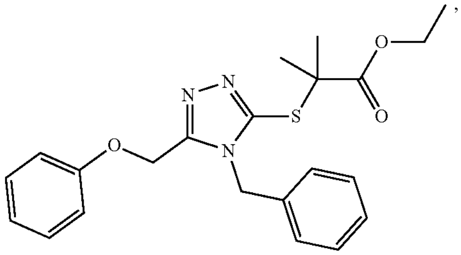
,
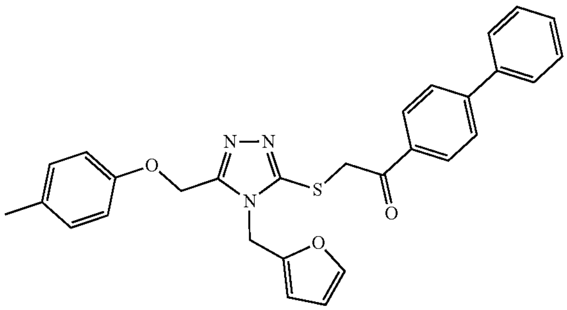
,
-continued
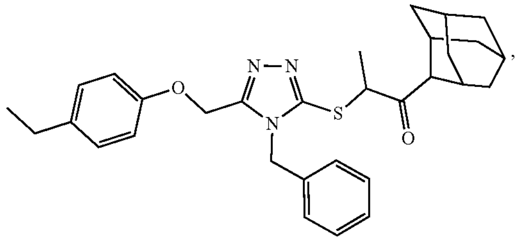
, and
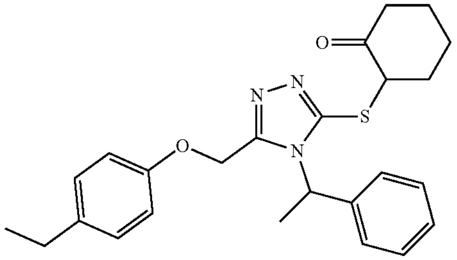
a pharmaceutically acceptable salt thereof.
3. The method of claim 2, wherein the cancer is selected from the group consisting of colorectal cancer, hepatocellular cancer, melanoma, liver cancer, breast cancer, prostate cancer, and leukemia.
* * * * *